United States Patent
Cura et al.

(10) Patent No.: US 12,325,875 B2
(45) Date of Patent: Jun. 10, 2025

(54) METABOLIC ENZYME ACTIVITY AND DISULFIDE BOND REDUCTION DURING PROTEIN PRODUCTION

(71) Applicant: Bristol-Myers Squibb Company, Princeton, NJ (US)

(72) Inventors: Anthony Joseph Cura, Ayer, MA (US); Xuankuo Xu, Boxborough, MA (US); Zhengjian Li, Sudbury, MA (US); Sanchayita Ghose, Acton, MA (US); Susan Egan, Stow, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1278 days.

(21) Appl. No.: 16/980,607

(22) PCT Filed: Mar. 15, 2019

(86) PCT No.: PCT/US2019/022496
§ 371 (c)(1),
(2) Date: Sep. 14, 2020

(87) PCT Pub. No.: WO2019/178489
PCT Pub. Date: Sep. 19, 2019

(65) Prior Publication Data
US 2021/0010055 A1 Jan. 14, 2021

Related U.S. Application Data

(60) Provisional application No. 62/644,181, filed on Mar. 16, 2018.

(51) Int. Cl.
*C12Q 1/32* (2006.01)
*C07K 16/00* (2006.01)
*C12Q 1/26* (2006.01)

(52) U.S. Cl.
CPC ............... *C12Q 1/32* (2013.01); *C07K 16/00* (2013.01); *C12Q 1/26* (2013.01); *G01N 2333/90212* (2013.01); *G01N 2333/904* (2013.01); *G01N 2440/20* (2013.01)

(58) Field of Classification Search
None
See application file for complete search history.

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 5,122,469 A | 6/1992 | Mather et al. |
| 5,633,162 A | 5/1997 | Keen et al. |
| 5,658,754 A | 8/1997 | Kawasaki |
| 5,721,121 A | 2/1998 | Etcheverry et al. |
| 6,291,159 B1 | 9/2001 | Winter |
| 6,657,103 B1 | 12/2003 | Kucherlapati et al. |
| 2004/0082764 A1 | 4/2004 | Kunz et al. |

FOREIGN PATENT DOCUMENTS

| | | | | |
|---|---|---|---|---|
| CA | 2890875 | * | 5/2014 | ......... C12N 15/1135 |
| EP | 0171496 A2 | | 2/1986 | |
| EP | 0173494 A2 | | 3/1986 | |
| EP | 0239400 A2 | | 9/1987 | |
| GB | 2177096 B | | 5/1989 | |
| JP | 2012507499 | * | 3/2012 | .............. A61P 37/06 |
| WO | WO 92/06193 A1 | | 4/1992 | |
| WO | WO 2009/155504 | * | 12/2009 | ................ A61P 3/10 |
| WO | WO 2011/067377 | * | 6/2011 | ......... G01N 33/6893 |
| WO | WO 2014/071406 | * | 5/2014 | ........... C12Q 1/6886 |
| WO | WO 2017/196810 A1 | | 11/2017 | |
| WO | WO 2019/018770 | * | 1/2019 | .............. C07K 16/00 |

OTHER PUBLICATIONS

Cura et al. 'Differential expression and activity of metabolic enzymes in cell culture fluid correlates with increased disulfide reduction of mAb products.' Abstracts of Papers, 255th ACS National Meeting & Exposition, New Orleans, LA, United States, Mar. 18-22, 2018 (2018), BIOT-14 Publisher: ACS Washington, DC.*

Barnes, D., and Sato, G., "Serum-free cell culture: a unifying approach," *Cell*, 22(3):649. Elsevier, Netherlands (1980).

Du, C., et al., "Using hydrogen peroxide to prevent antibody disulfide bond reduction during manufacturing process," *MABS*, 10(3):500-510, Taylor & Frances, LLC, United Kingdom (2018).

Graham, F. L., et al., "Characteristics of a Human Cell Line Transformed by DNA from Human Adenovirus Type 5," *J. Gen Virol.*, 36:59, Society for General Microbiology, London, United Kingdom (1977).

Handlogten, M., et al., "Glutathione and thioredoxin systems contribute to recombinant monoclonal antibody interchain disulfide bond reduction during bioprocessing," *Biotechnology and Bioengineering*, 114(7):1469-1477, John Wiley & Sons, Inc., New Jersey (2017).

(Continued)

*Primary Examiner* — Nora M Rooney
(74) *Attorney, Agent, or Firm* — Sterne, Kessler, Goldstein & Fox P.L.L.C.

(57) ABSTRACT

The present disclosure relates to the use of host cell protein biomarkers to assess disulfide bond reduction in compositions comprising a protein of interest. In some embodiments, the disclosure relates to methods of predicting the occurrence of disulfide bond reduction or low molecular weight protein species in compositions comprising a protein of interest, wherein the expression or activity level of at least one host cell protein is measured and provides a benchmark value associated with the occurrence of disulfide bond reduction or low molecular weight species of said protein of interest. In some embodiments, the disclosure relates to methods of producing a protein of interest, wherein host cells capable of producing the protein of interest are cultured, the expression or activity level of at least one host cell protein is measured, and downstream isolation of the protein of interest is informed by the host cell protein measurements.

20 Claims, 19 Drawing Sheets

(56) References Cited

OTHER PUBLICATIONS

International Search Report and Written Opinion for International Application PCT/US2019/022496, European Patent Office, Netherlands, mailed Aug. 13, 2019, 21 pages.

Jones, P.T., et al., "Replacing the complementarity-determining regions in a human antibody with those from a mouse," *Nature*, 321:522-525, Springer Nature, United Kingdom (1986).

Kao, Y-H. et al., "Mechanism of Antibody Reduction in Cell Culture Production Process," *Biotechnology and Bioengineering*, 107(4):622-632, John Wiley & Sons, Inc., New Jersey (2010).

Koterba, K., et al., "Thioredoxin 1 is responsible for antibody disulfide reduction in CHO cell culture," *Journal of Biotechnology*, 157(1):261-267, Elsevier, Netherlands (2011).

Kozbor, D., and Roder, J.C., "The production of monoclonal antibodies from human lymphocytes," *Immunology Today*, 4(3):72-79, Elsevier, Netherlands (1983).

Lee, J. et al., "Control of fed-batch fermentations," *Biotechnol. Adv.*, 17(1):29-48, Elsevier, Netherlands (1999).

Mather, J.P., et al., "Culture of Testicular Cells in Hormone-Supplemented Serum-Free Medium," *Annals N.Y. Acad. Sci.*, 383(1):44-68, New York Academy of Science, United States (1982).

Mather, P. J., "Establishment and Charcterization of Two Distinct Mouse Testicular Epithelial Cell Lines," *Biology of Reproduction*, 23:243-251, Oxford University Press, United Kingdom (1980).

Morrison, S.L., et al., Chimeric human antibody molecules: Mouse antigen-binding domains with human constant region domains, *Proc. Natl. Acad. Sci. USA*, 81: 6851, United States National Academy of Sciences, United States (1985).

Olsson, L. and Kaplan, H.S., "[1] Human-human monocolonal antibody producing hybridomas: Technical aspects," *Meth. Enzymol.*, 92:3-16, Elsevier, Netherlands (1982).

Presta, L.G., "Antibody engineering," *Curr. Op. Struct. Biol.* 2(4):593-596, Elsevier, Netherlands (1992).

Riechmann, L., et al., "Reshaping human antibodies for therapy," *Nature*, 332:323-329, Springer Nature, United Kingdom (1988).

Takeda, S., et al., "Construction of chimaeric processed immunoglobulin genes containing mouse variable and human constant region sequences," *Nature*, 314:452-454, Springer Nature, United Kingdom (1985).

Teng, N.N.H., et al., "Construction and testing of mouse-human heteromyelomas for human monoclonal antibody production," *Proc. Natl. Acad Sci. USA.*, 80, 7308-7312, United States National Academy of Sciences, United States (1983).

Urlaub, G. and Chasin, L.A., "Isolation of Chinese hamster cell mutants deficient in dihydrofolate reductase activity," *Proc. Natl. Acad. Sci. USA*, 77(7):4216-4220, United States National Academy of Sciences, United States (1980).

Wlaschin, K. F. and Hu, W-S., "Fedbatch Culture and Dynamic Nutrient Feeding," *Adv. Biochem Engin/Biotechnol*, 101:43-74, Springer-Verlag Berlin Heidelberg (2006).

Skulj, M., et al., "Reduction in C-terminal amidated species of recombinant monoclonal antibodies by genetic modification of CHO cells," BMC Biotechnology 14:76, BioMed Central. United Kingdom (Aug. 2014).

Darja, O., et al., "Responses of CHO cell lines to increased pCO2 at normal (37 C) and reduced (33 C) culture temperatures," Journal of Biotechnology 219:98-109, Elsevier, Netherlands (Feb. 2016).

\* cited by examiner

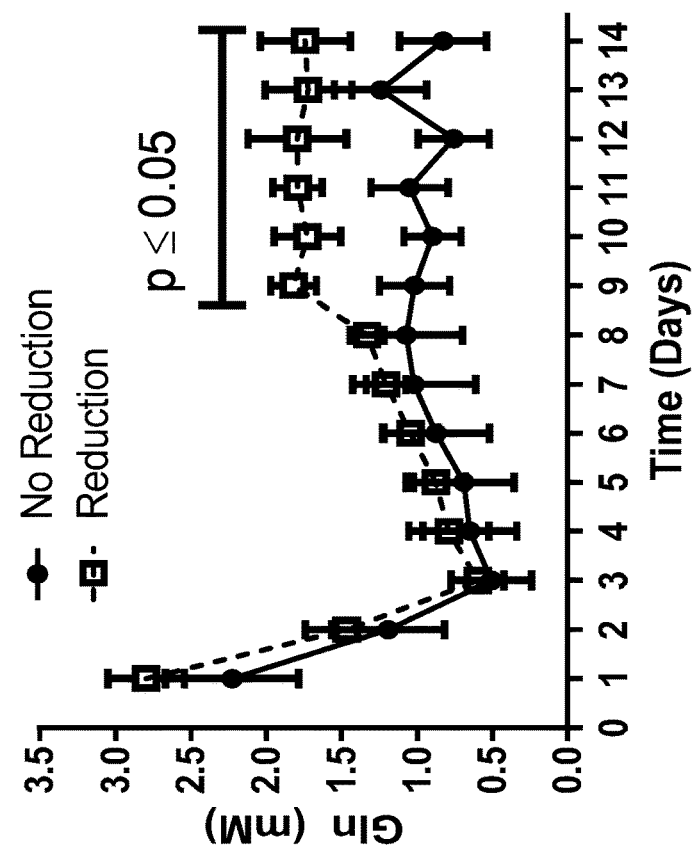
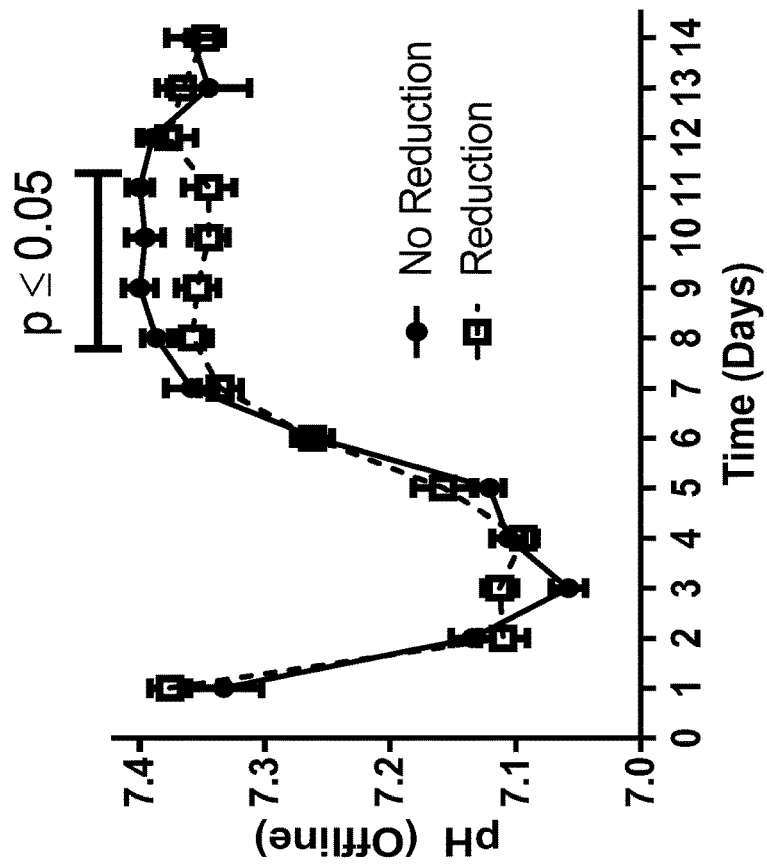
FIG. 1A
FIG. 1B

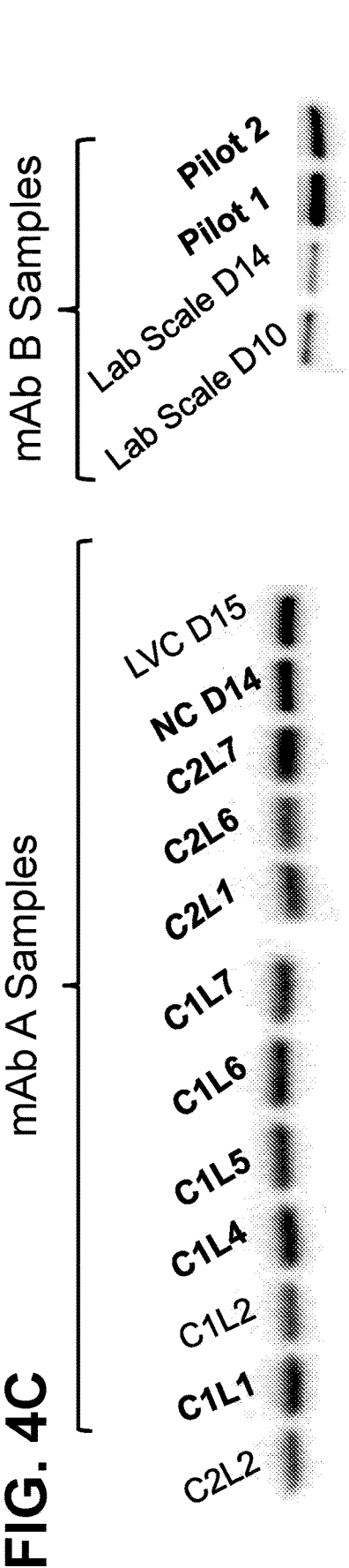
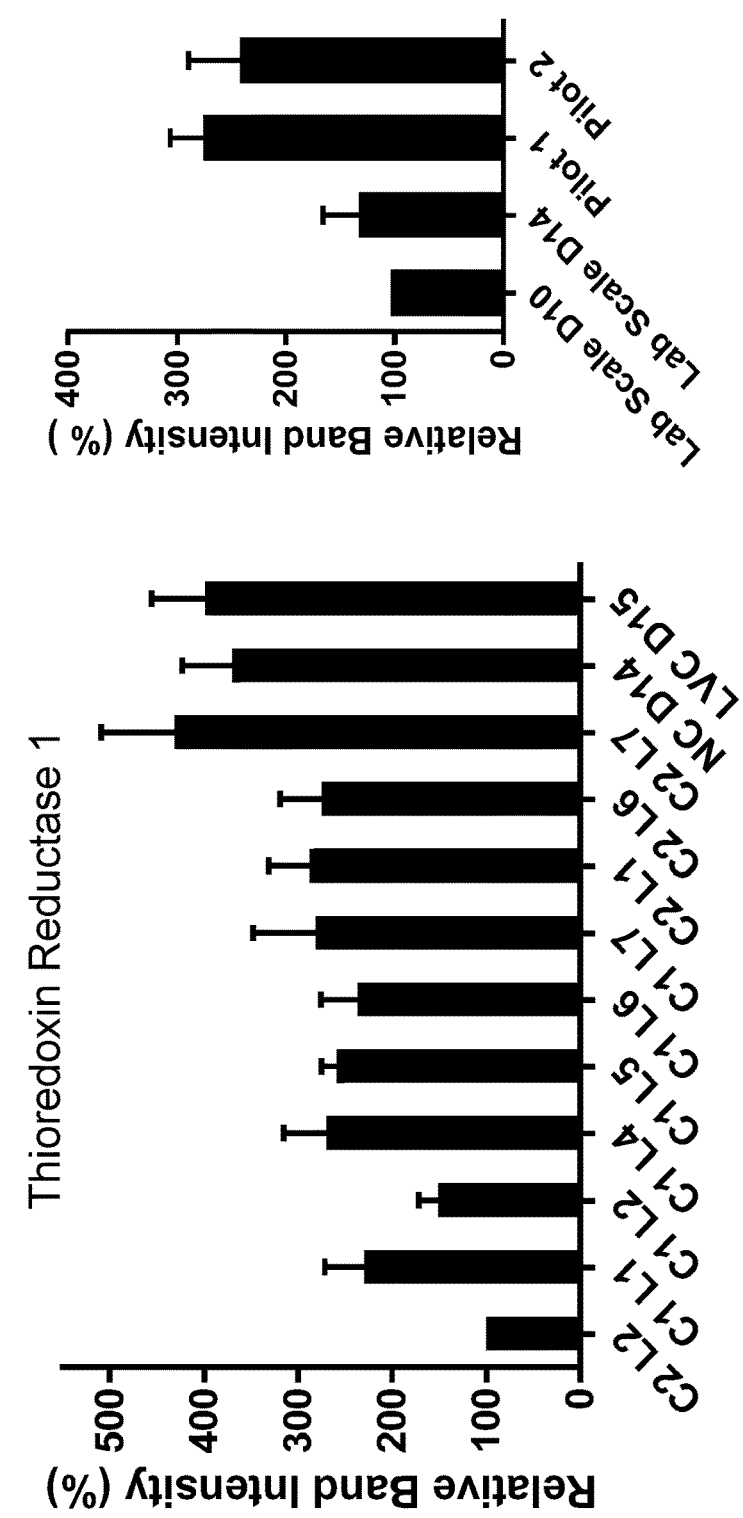
FIG. 4C
FIG. 4D

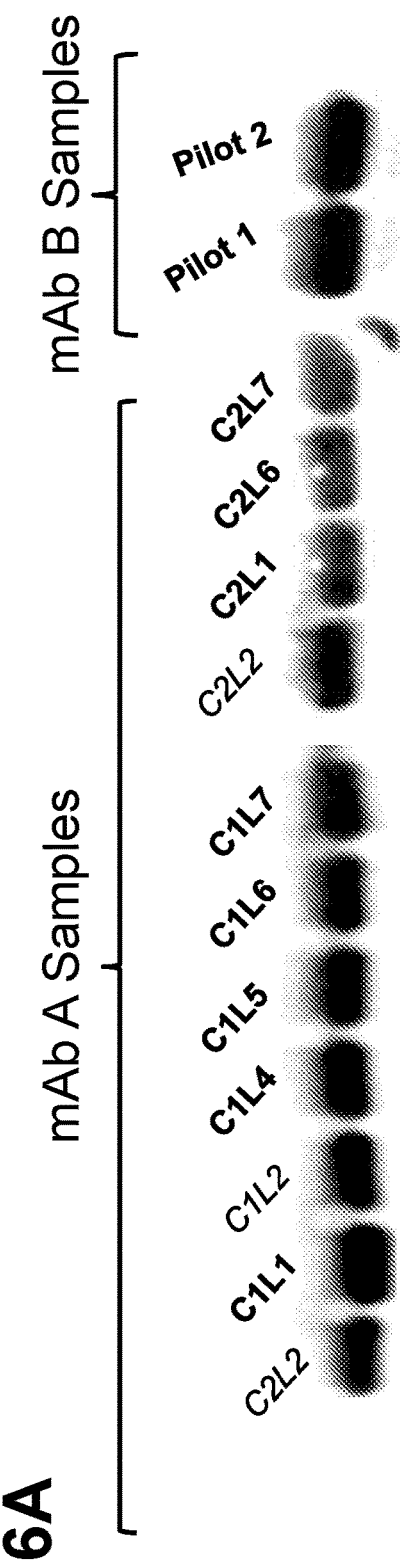
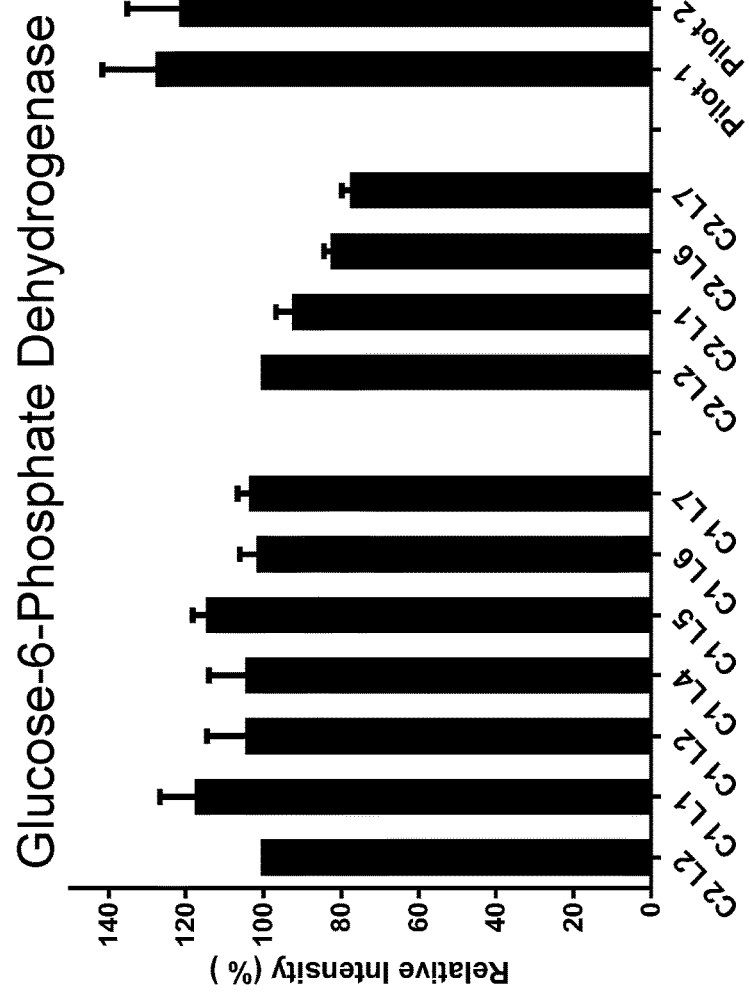
FIG. 6A
FIG. 6B

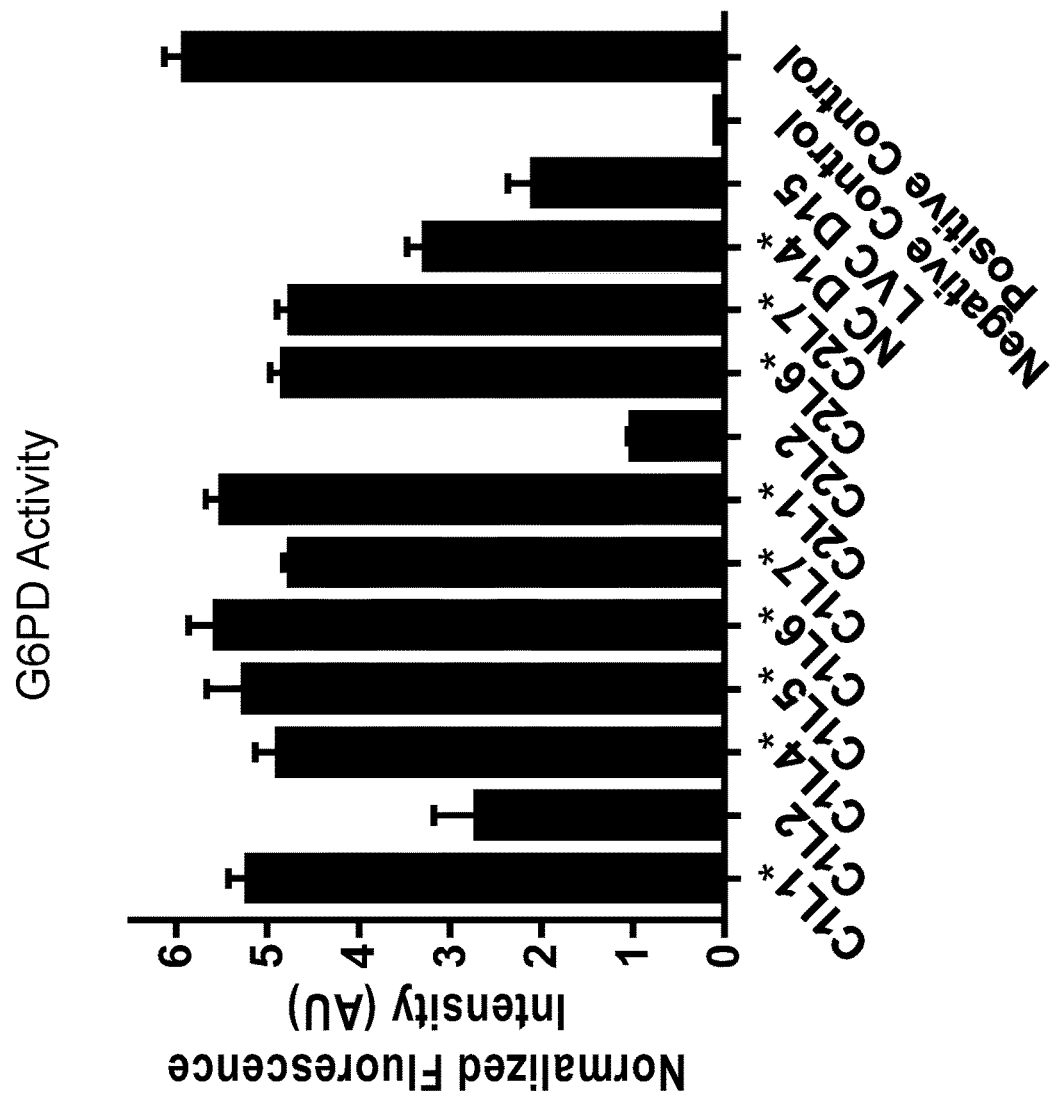

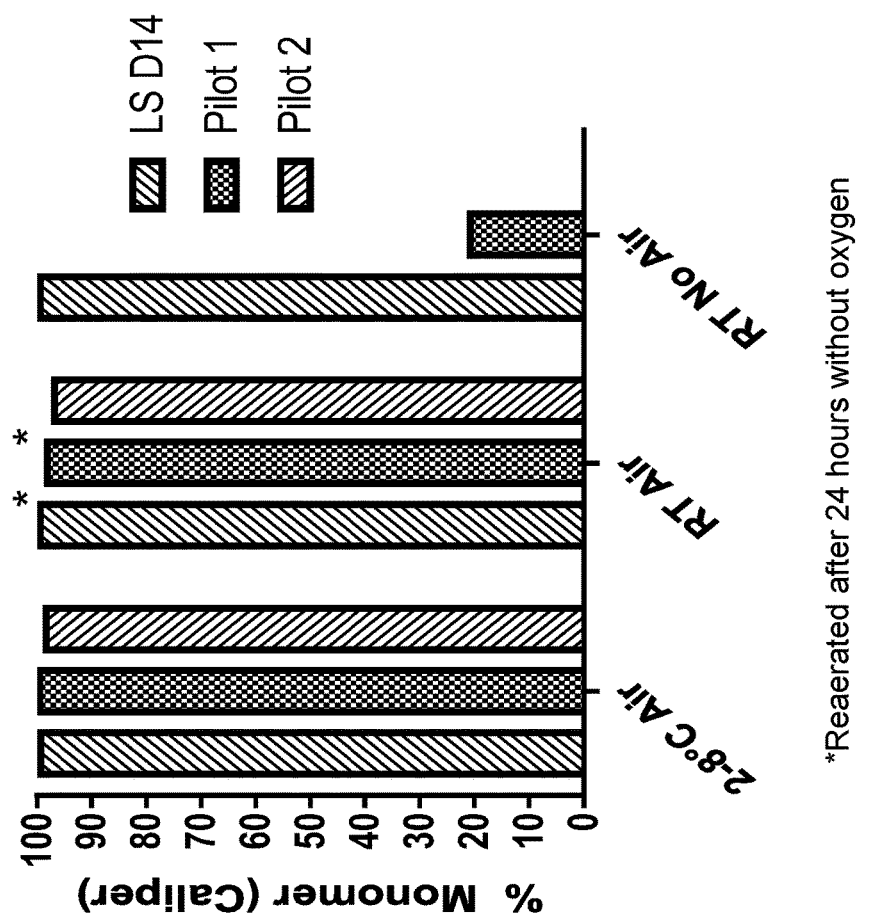
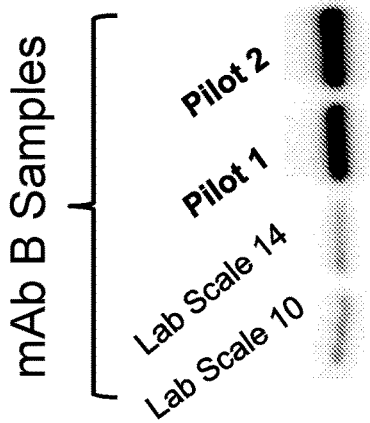
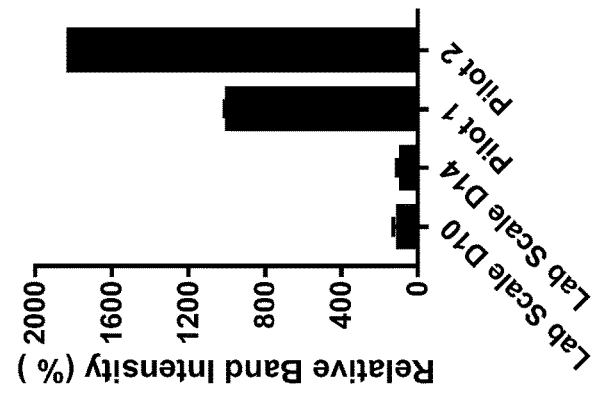

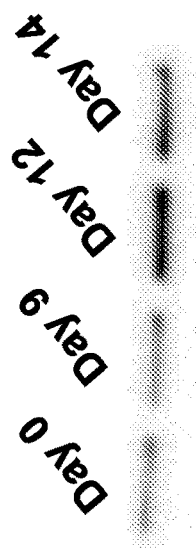
FIG. 11C Control
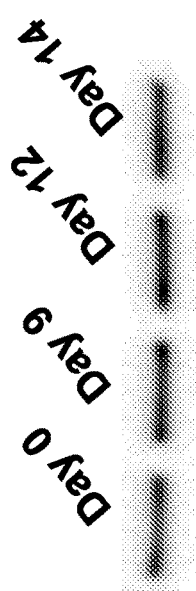
FIG. 11E Reducing 1
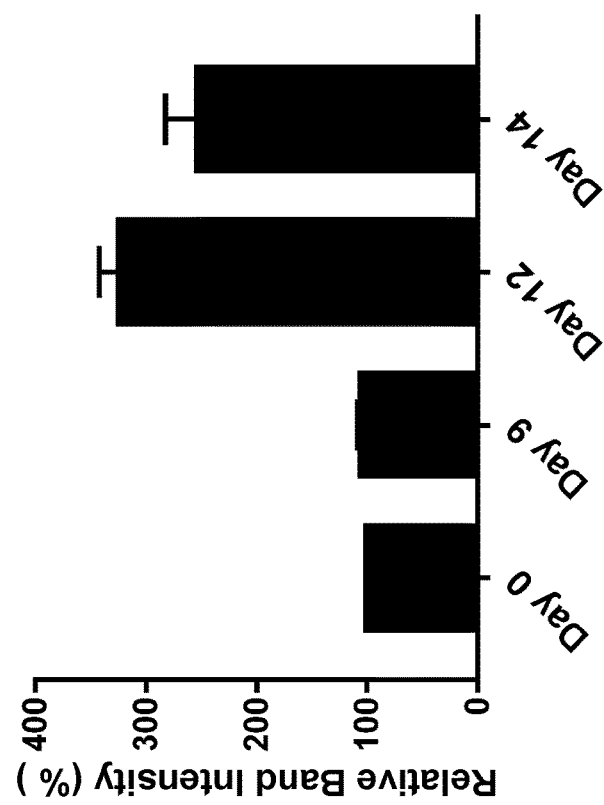
FIG. 11D
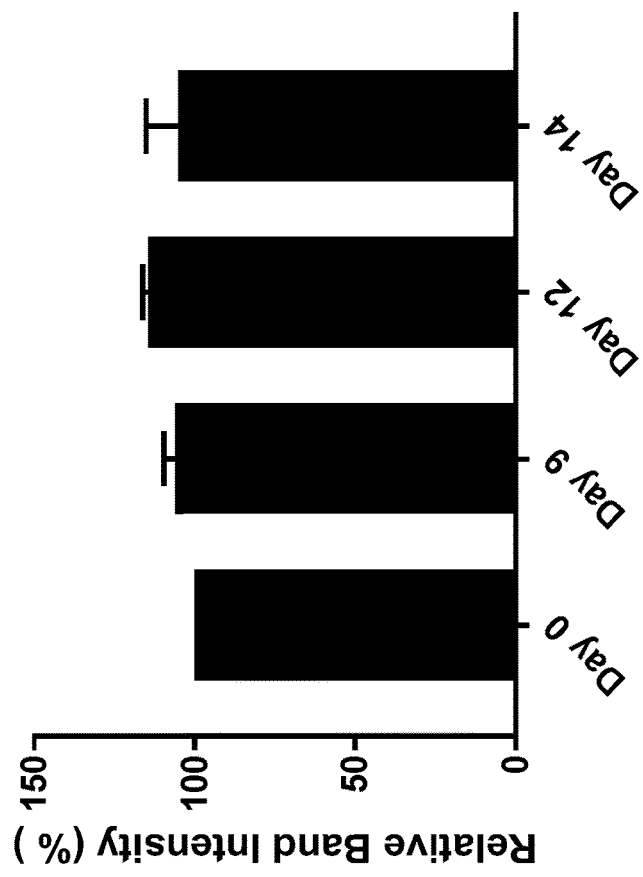
FIG. 11F

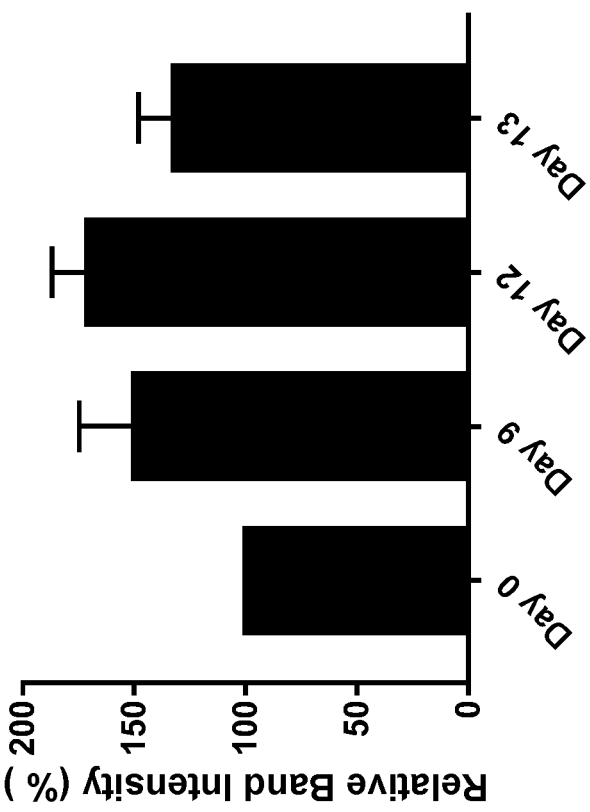
FIG. 11I  FIG. 11J
FIG. 11G  FIG. 11H
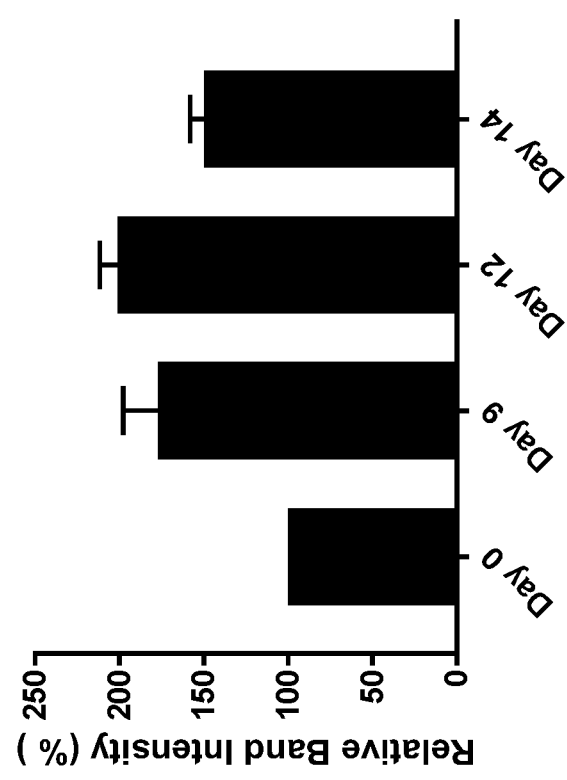

METABOLIC ENZYME ACTIVITY AND DISULFIDE BOND REDUCTION DURING PROTEIN PRODUCTION

CROSS-REFERENCE TO RELATED APPLICATIONS

This application is the National Stage of International Application Number PCT/US2019/022496, filed Mar. 15, 2019, which claims the benefit of U.S. Provisional Application No. 62/644,181, filed Mar. 16, 2018, each of which is incorporated by reference herein.

BACKGROUND OF THE DISCLOSURE

With the increased demand for biopharmaceuticals to target a wide range of diseases, modern development efforts are heavily focused on maximizing monoclonal antibody (mAb) product yield while controlling process-related impurities. One of the unanticipated side-effects of higher host-cell density, titer, and productivity is the increased presence of host-cell proteins (HCP) in harvested cell culture fluid (HCCF). Not only does increased HCP further challenge downstream impurity clearance efforts, but can also impact mAb stability even before purification begins. One such consequence of increased HCP is the thioredoxin (Trx)-induced disulfide bond reduction of intact mAbs and subsequent formation of low molecular weight species (LMW). Disulfide reduction s a direct risk to product stability, potency, and patient safety; and though the enzymatic mechanism of reduction is well established, the cellular mechanisms leading to increased reductase activity and expression in HCCF remain unclear. Further, batch to batch variability in disulfide reduction makes studying such mechanisms a challenge.

Accordingly, there is a need in the art for identifying markers associated with disulfide bond reduction in cell culture and the development of methods that utilize such markers to reliably predict disulfide bond reduction risk prior to harvest.

SUMMARY OF THE DISCLOSURE

In one embodiment, the present disclosure relates to a method of predicting the occurrence of disulfide bond reduction in a composition comprising a protein of interest, the method comprising measuring the expression or activity level of at least one host cell protein, which is not said protein of interest, or measuring the level of at least one bioreactor metabolite, wherein a host cell protein expression, activity, or bioreactor metabolite level above a benchmark value is associated with the occurrence of disulfide bond reduction of said protein of interest.

In one embodiment, the present disclosure relates to a method of predicting the occurrence of disulfide reduction of intact monomeric protein species in a composition comprising a protein of interest, the method comprising measuring the expression or activity level of at least one host cell protein, which is not said protein of interest, or measuring the level of at least one bioreactor metabolite, wherein a host cell protein expression, activity, or bioreactor metabolite level above a benchmark value is associated with the occurrence of disulfide reduction of intact monomeric protein species of said protein of interest.

In one embodiment, the present disclosure relates to a method of producing a protein of interest, the method comprising: a) culturing host cells capable of producing said protein of interest; b) measuring the expression level or activity level of at least one host cell protein, which is not said protein of interest, or measuring the level of at least one bioreactor metabolite; and c) isolating said protein of interest if either the host cell protein expression, activity, or bioreactor metabolite level is below a benchmark value.

In one embodiment, the present disclosure relates to a method of producing an antibody of interest, the method comprising: a) culturing host cells capable of producing said antibody; b) measuring the expression level or activity level of at least one host cell protein, which is not said antibody of interest, or measuring the level of at least one bioreactor metabolite; c) altering at least one growth condition of said host cells if either the host cell protein expression, activity, or bioreactor metabolite level is above a benchmark value; and d) isolating said antibody of interest.

In some embodiments, a composition comprising a protein of interest is produced from a cell culture. In some embodiments, the cell culture comprises a host cell capable of producing said protein of interest.

In some embodiments, the expression level of a host cell protein is determined. In some embodiments, the expression level of at least two host cell proteins is determined. In some embodiments, the expression level of at least three host cell proteins is determined.

In some embodiments, the expression level of at least one host cell protein involved in the oxidative stress pathway, the heat shock protein pathway, and/or the hypoxia-induced stress pathway is determined.

In some embodiments, the activity level of a host cell protein is determined. In some embodiments, the activity level of at least two host cell proteins is determined.

In some embodiments, the level of a bioreactor metabolite is measured. In some embodiments, the level of at least two bioreactor metabolites are measured. In some embodiments, the level of at least three bioreactor metabolites are measured.

In some embodiments, at least one host cell protein is selected from the group consisting of: thioredoxin, thioredoxin reductase, peroxiredoxin, dihydrofolate reductase, glucose-6-phosphate dehydrogenase (G6PD), 6-phosphogluconate dehydrogenase (6PGD), and glyceraldehyde-3-phosphate dehydrogenase (GAPDH). In some embodiments, at least one host cell protein is selected from the group consisting of: thioredoxin, thioredoxin reductase, and glyceraldehyde-3-phosphate dehydrogenase (GAPDH). In some embodiments, at least one host cell protein is thioredoxin reductase or glucose-6-phosphate dehydrogenase (G6PD).

In some embodiments, the expression level of at least one host cell protein is measured, the level of activity of at least one host cell protein is measured, and/or the level of at least one bioreactor metabolite is measured.

In some embodiments, the activity level of at least one host cell protein involved in the oxidative stress pathway, the heat shock protein pathway, and/or the hypoxia-induced stress pathway is determined.

In some embodiments, the expression level is measured in a cell culture fluid. In some embodiments, the expression level is measured intracellularly. In some embodiments, the intracellular expression level is measured in a cell culture lysate. In some embodiments, the expression level is measured by western blot analysis or qPCR analysis.

In some embodiments, the thioredoxin reductase activity level is measured by thioredoxin reductase activity assay. In some embodiments, the glucose-6-phosphate dehydrogenase (G6PD) activity level is measured by G6PD activity assay. In some embodiments, the glyceraldehyde-3-phosphate dehydrogenase (GAPDH) activity level is measured by GAPDH activity assay.

In some embodiments, the level of bioreactor metabolite is measured in a cell culture fluid.

In some embodiments, the occurrence of disulfide bond reduction or low molecular weight protein species is detected by capillary electrophoresis.

In some embodiments, the expression level of thioredoxin is measured, and the benchmark value is a thioredoxin relative band intensity of about 200%, as determined by western blot analysis. In some embodiments, the expression level of thioredoxin reductase is measured, and the benchmark value is a thioredoxin reductase relative band intensity of about 160%, as determined by western blot analysis. In some embodiments, the expression level of GAPDH is measured, and the benchmark value is a GAPDH relative band intensity of about 140%, as determined by western blot analysis.

In some embodiments, the activity level of thioredoxin reductase is measured, and the benchmark value is a relative TrxR activity (A.U.) of 1.0 after 60 minutes, as determined by thioredoxin reductase activity assay. In some embodiments, the activity level of glucose-6-phosphate dehydrogenase (G6PD) is measured, and the benchmark value is a normalized resorufin fluorescence (AU) of 3.0, as determined by G6PD activity assay. In some embodiments, the activity level of glyceraldehyde-3-phosphate dehydrogenase (GAPDH) is measured and normalized to protein concentration.

In some embodiments, a protein of interest is an antibody or antigen-binding fragment thereof. In some embodiments, the antibody is a chimeric, humanized or human monoclonal antibody. In some embodiments, the IgG subtype is IgG1, IgG2, IgG3, or IgG4.

In some embodiments, a host cell is a mammalian cell. In some embodiments, a host cell is a Chinese Hamster Ovary (CHO) cell.

In some embodiments, a cell culture is a batch, fed batch, or perfusion culture. In some embodiments, the initial density of mammalian cells is at least $2\times10^2$ cells/mL; at least $2\times10^3$ cells/mL; at least $2\times10^4$ cells/mL; at least $2\times10^5$ cells/mL; at least $2\times10^6$ cells/mL; at least $5\times10^6$ cells/mL; or at least $10\times10^6$ cells/mL. In some embodiments, the cells are grown for a period of time sufficient to achieve a desired viable cell density of at least 1, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95 or at least 99 percent of maximal viable cell density.

In some embodiments, cells are grown in a bioreactor. In some embodiments, the bioreactor is an N−1 seed bioreactor. In some embodiments, the bioreactor is used for large-scale production of the protein of interest. In some embodiments, the bioreactor is a 1,000 L, 2,500 L, 5,000 L, 8,000 L, 10,000 L, 12,000 L, or 15,000 L bioreactor.

In some embodiments, viable cell density of the culture is measured on a periodic basis. In some embodiments, the lactate level of the culture is measured on a periodic basis. In some embodiments, the ammonium level of the culture is measured on a periodic basis. In some embodiments, the titer of a protein of interest is measured on a periodic basis. In some embodiments, the osmolarity of the culture is measured on a periodic basis. In some embodiments, the amount of dissolved oxygen in the culture is measured on a periodic basis. In some embodiments, the $pCO_2$ level of the culture is measured on a periodic basis. In some embodiments, the pH of the culture is measured on a periodic basis. In some embodiments, the glutamine level of the culture is measured on a periodic basis. In some embodiments, the glutamate level of the culture is measured on a periodic basis. In some embodiments, the glucose level of the culture is measured on a periodic basis. In some embodiments, the expression or activity level of the host cell protein is measured on a periodic basis.

In some embodiments, measurements are taken during growth phase of the cell culture. In some embodiments, measurements are taken during the transition phase of the cell culture. In some embodiments, measurements are taken during the production phase of the cell culture. In some embodiments, measurements are taken daily. In some embodiments, the expression or activity level of a host cell protein is measured on day 1, 2, 3, 4, 5, 6, 7, 8, 9, 10, 11, 12, 13, 14, 15, 16, 17, 18, 19, 20, or 21 following the start of cell culture. In some embodiments, the host cell protein is a CHO cell protein.

BRIEF DESCRIPTION OF THE DRAWINGS

FIGS. 1A-1J show trends for 12 monitored upstream parameters in manufacturing scale and laboratory-scale runs for a monoclonal antibody. Runs showing disulfide bond reduction or no disulfide bond reduction were averaged and are presented as the mean+SEM for each parameter. Differences between samples showing disulfide bond reduction or no disulfide bond reduction were analyzed by two-tailed paired t-test. For each sample, FIG. 1A shows the bioreactor pH profile, FIG. 1B shows the bioreactor glutamine profile, FIG. 1C shows the bioreactor lactate profile, FIG. 1D shows the bioreactor ammonium profile, FIG. 1E shows the bioreactor viable cell density, FIG. 1F shows the bioreactor percent cell viability, FIG. 1G shows the bioreactor dissolved oxygen content, FIG. 1H shows the bioreactor $pCO_2$ content, FIG. 1I shows the bioreactor glutamate profile, and FIG. 1J shows the bioreactor glucose profile.

FIG. 2A shows the % monomer and cell culture parameters associated with normal conditions at day 14, and FIG. 2B shows the % monomer and cell culture parameters associated with low viability conditions at day 15. Sample were stored at 2-8° C. or room temperature (RT) with no air or with air head space for ≥24 hours.

FIGS. 4A-4D show the expression of thioredoxin 1 and thioredoxin reductase 1 in samples harvested from bench, pilot, and manufacturing scale runs for two monoclonal antibodies. FIG. 4A shows a western blot for thioredoxin 1, with band densities quantitated in FIG. 4B. FIG. 4C shows a western blot for thioredoxin reductase 1, with band densities quantitated in FIG. 4D. Bolded samples in FIGS. 4A and 4C demonstrated disulfide bond reduction. Blots were run in triplicate for each sample, and band densities represent the mean+SEM for three separate blots.

FIGS. 6A and 6B show the expression of glucose-6-phosphate dehydrogenase (G6PD) in samples harvested from manufacturing and pilot scale runs for two monoclonal antibodies. FIG. 6A shows a western blot for G6PD, with band densities quantitated in FIG. 6B. Bolded samples in FIG. 6A demonstrated disulfide bond reduction. Blots were run in triplicate for each sample, and band densities represent the mean+SEM for three separate blots.

FIG. 7 shows the results of a glucose-6-phosphate dehydrogenase (G6PD) activity assay for samples harvested from manufacturing and laboratory-scale runs for a monoclonal antibody. Boxed samples demonstrated disulfide bond reduction, while asterisked samples did not.

FIG. 8A shows a western blot for GAPDH, with band densities quantitated in FIG. 8B. Blots were run in triplicate for each sample, and band densities represent the mean+SEM for three separate blots.

FIGS. 9A-9C show the expression of glyceraldehyde-3-phosphate dehydrogenase (GAPDH) and the extent of disulfide bond reduction in samples harvested from lab scale and pilot runs for a second monoclonal antibody. FIG. 9A shows a western blot for GAPDH, with band densities quantitated in FIG. 9B. FIG. 9C shows the extent of disulfide bond reduction is samples from lab scale and pilot runs which were stored at 2-8° C. or at room temperature (RT) with no air or with an air overlay for 24 hours.

FIG. 10A shows the relative GAPDH activity and FIG. 10B shows the relative GAPDH activity normalized to protein concentration.

FIGS. 11A-11J shows the results of Glyceraldehyde-3-Phosphate Dehydrogenase Gene and Protein Expression. FIGS. 11A and 11B: mRNA from Control, Reducing 1, Reducing 2, and Reducing 3 samples were analyzed for GAPDH gene expression by q-RT-PCR. Relative expression was normalized to Control condition and results were plotted over time (11A) or for the day 7 and day 9 cell pellet samples (11B). Relative expression results represent the mean+SEM for each sample tested. FIGS. 11C, 11E, 11G, and 11I shows Western Blots for GAPDH in mAb B cell pellets cultured under Control, Reducing 1, Reducing 2, or Reducing 3. Band densities were quantitated and normalized to the day 0 cell pellet for each condition tested (11D, 11F, 11H, 11J, respectively) Blots were run in triplicate for each sample, and band densities represent the mean+SEM for three separate blots.

FIG. 12A: HCCF from bench scale production bioreactors cultured under Control, Reducing 1, Reducing 2, or Reducing 3 were incubated at 2-8° C. with dissolved oxygen (DO, solid bars) or ambient temperature without dissolved oxygen (NO DO, checkered bars) for 5 days. FIG. 12A shows the percent amount of intact monomer present in each sample. FIG. 12B: Cell samples were pulled from each production bioreactor (Control, Reducing 1, Reducing 2, and Reducing 3) at the times indicated, and supernatants were analyzed for lactate and pyruvate content. The concentration of lactate was divided by the concentration of pyruvate to yield the lac/pyr ratio for each bioreactor over time. Lac/pyr ratios were normalized to Control condition and plotted as relative % increase in lac/pyr ratio versus time.

DETAILED DESCRIPTION OF THE DISCLOSURE

Definitions of General Terms and Expressions

Figure 1D:
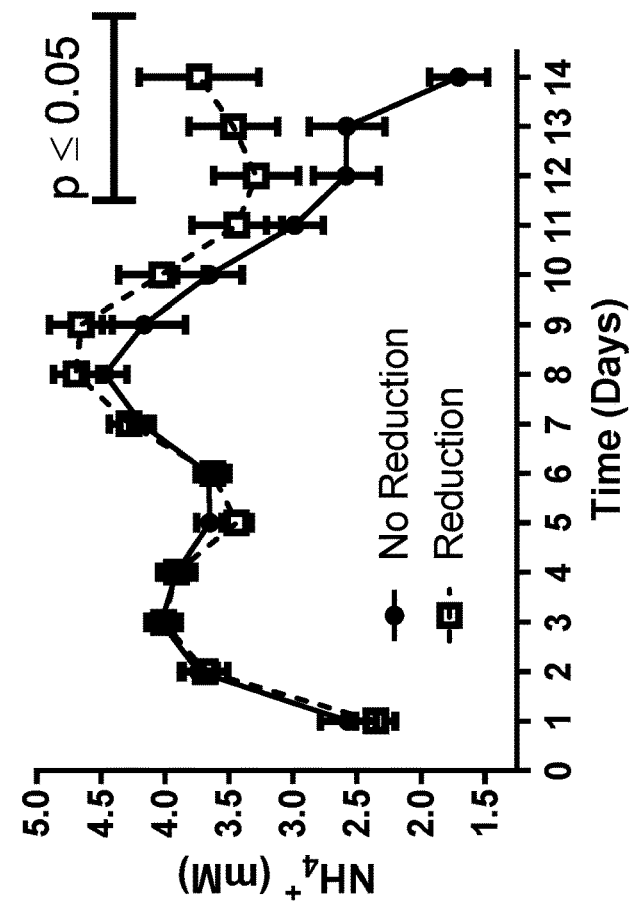

In order that the present disclosure may be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one tenth and one hundredth of an integer), unless otherwise indicated.

The term "disulfide bond reduction" as used herein refers to the chemical process by which a sulfur-sulfur bond is broken and replaced by a hydrogen-sulfur bond. The interconversion of disulfide groups (characterized by an S—S bond) and thiols (characterized by an H—S bond) represents a redox reaction, wherein the thiol represents the reduced state and the disulfide represents the oxidized state. In proteins, disulfide linkages between two cysteine residues often contribute to the protein's three-dimensional structure and stability; thus, the reduction of disulfide linkages can result in the formation of low molecular weight protein species. The extent of disulfide bond reduction and the presence of low molecular weight species can be measured by known methods, such as capillary electrophoresis. Such measurements are often presented as the % monomer in a sample, with a % monomer of less than 95% typically indicating the presence of disulfide bond reduction.

The terms "cell culture" and "culture" include any combination of cells and medium. The methods of the present disclosure contemplate, without limitation, perfusion cell culture, batch culture and fed-batch cell culture.

As used herein, the terms "perfuse", "perfusion" and "perfusion culture" are used interchangeably to refer to a method of culturing cells, wherein additional fresh medium is provided to the culture and spent medium is removed from the culture. Perfusion is initiated after the culture is seeded and can occur either continuously or intermittently, as desired, over a period of time. The fresh medium added during perfusion typically provides nutritional supplements for the cells that have been depleted during the culturing process. Perfusion also allows for removal of cellular waste products and toxic byproducts from the cell culture. Perfusion is performed during the growth phase of the cells, but can also be continued after the cells have been transferred to a fed-batch cell culture.

The term "batch culture" as used herein refers to a method of culturing cells in which all the components that will ultimately be used in culturing the cells, including the medium as well as the cells themselves, are provided at the beginning of the culturing process. A batch culture is typically stopped at some point and the cells and/or components in the medium are harvested and optionally purified.

As used herein, the term "fed-batch culture" refers to a method of culturing cells, wherein the cell culture is supplemented with fresh medium, i.e., the cells are "fed" with new medium while spent medium is not removed. Typically, a "fed-batch" culture process is performed in a bioreactor and additional components (e.g., nutritional supplements) are added to the culture at some time after initiation of the culture process. The controlled addition of nutrients directly affects the growth rate of the culture and allows for avoidance of the build-up of overflow metabolites (see, for example, Wlaschin, K. F. et al., "Fedbatch culture and dynamic nutrient feeding," *Cell Culture Engineering,* 101: 43-74 (2006) and Lee, J. et al., "Control of fed-batch fermentations," *Biotechnol. Adv.,* 17:29-48 (1999)). A fed-batch culture is typically terminated at some point and the cells and/or components in the medium are harvested and optionally purified.

As used herein, the terms "inoculation", "inoculum", and "seeding" refer to the addition of cells to starting medium to begin the culture.

As used herein, the term "cell density" refers to the number of cells in a given volume of medium. Cell density can be monitored by any technique known in the art, including, but not limited to, extracting samples from a culture and analyzing the cells under a microscope, using a commercially available cell counting device or by using a commercially available suitable probe introduced into the bioreactor itself (or into a loop through which the medium and suspended cells are passed and then returned to the bioreactor).

As used herein the terms "super high cell density" and "high cell density" are used interchangeably and refer to a cell density of at least about $40 \times 10^6$ cells/mL in an N−1 perfusion bioreactor. Known cell culture techniques may involve growing cells to a "first critical level" (i.e., "a point during the cell cycle growth phase when the cell viability may be affected by the increased concentration of waste productions (e.g., cell growth inhibitors and toxic metabolites, e.g., lactate, ammonium, etc.)" before perfusing the cell culture and obtaining roughly 5 to 40 million cells/mL). In contrast, cells grown according to the methods of the present disclosure may reach a high cell density. In some embodiments, cells of the present disclosure are grown to target cell densities of least above about 40, 45, 50, 55, 60, 65, 70, 75, 80, 90, 100, 110, 120, or $130 \times 10^6$ cells/mL. In particular embodiments, cells of the present disclosure are grown to target cell densities of about $60 \times 10^6$ cells/mL. In other embodiments, cells of the present disclosure are grown to target cell densities of about $40 \times 10^6$ cells/mL. High density seeding refers to inoculating cultures at about $5 \times 10^6$ cells/ml, about $10 \times 10^6$ cells/ml, about $15 \times 10^6$ cells/ml, about $20 \times 10^6$ cells/ml, or about $25 \times 10^6$ cells/ml. In certain embodiments, high density seeding refers to inoculating cultures at about $10 \times 10^6$ cells/ml.

As used herein, the term "viable cell density" or "VCD" refers to the number of live cells present in a given volume of medium under a given set of experimental conditions.

As used herein, the term "cell viability" refers to the ability of cells in culture to survive under a given set of conditions or experimental variations. The term as used herein also refers to that portion of cells that are alive at a particular time in relation to the total number of cells (e.g., living and dead) in the culture at that time.

As used herein, the "growth phase" of a cell culture refers to the phase during which the viable cell density at any time point is higher than at any previous time point.

As used herein, the "production phase" of a cell culture refers to the phase during which the cells produce significant amounts of protein, which accumulates for future processing.

As used herein, the "transition phase" of a cell culture refers to a phase between the growth and production phases in which cell culture conditions may be altered (e.g., by lowering the temperature of the cell culture). Typically, a transition phase is carried out for 24-48 hours prior to entering into the production phase.

As used herein, the term "cell integral" refers to the overall viable cell numbers during the course of a cell growth profile.

As used herein, the term "titer" refers to the total amount of protein produced by a cell culture, divided by a given amount of medium volume. In essence, the term "titer" refers to a concentration and is typically expressed in units of milligrams of polypeptide per liter of medium. Methods of the present disclosure may substantially increase polypeptide product titer, as compared to polypeptide product titers produced from other cell culture methods known in the art.

As used herein, the terms "media", "cell culture media" and "culture media", including grammatical variations thereof, are used interchangeably, and refer to the nutrient solution in which cells (for example, animal or mammalian cells) are grown in culture. Cell culture media is the physiochemical, nutritional, and hormonal environment for cells and typically includes at least one or more components from the following: an energy source (e.g., in the form of a carbohydrate such as glucose); essential amino acids, including the twenty basic amino acids plus cysteine; vitamins and/or other organic compounds typically required at low concentrations; lipids or free fatty acids (e.g., linoleic acid); and trace elements (e.g., inorganic compounds or naturally occurring elements that are typically required at very low concentrations, usually in the micromolar range). Media may be solid, gelatinous, liquid, gaseous or a mixture of phases and materials.

As used herein, the term "cell", refers to animal cells, mammalian cells, cultured cells, host cells, recombinant cells, and recombinant host cells. Such cells are generally cell lines obtained or derived from mammalian tissues which are able to grow and survive when placed in media containing appropriate nutrients and/or growth factors. The cells utilized in the methods of the present disclosure are generally animal or mammalian cells that can express and secrete, or that can be molecularly engineered to express and secrete, large quantities of a particular protein into the culture medium. In one embodiment, the protein produced by the cell can be endogenous or homologous to the cell. Alternatively, the protein is heterologous, i.e., foreign, to the cell.

The cells utilized in the methods of the present disclosure can be grown and maintained in any number of cell culture media, including those which are known in the art or are commercially available. One of ordinary skill in the art may opt to use one or more known cell culture media that is selected to maximize cell growth, cell viability, and/or protein production in a particular cultured host cell. Exemplary cell culture media include any media suitable for culturing cells that can express a protein of interest. In some embodiments, the media is chemically defined media.

Additionally, the cell culture media can optionally be supplemented to include one or more additional components, in appropriate concentrations or amounts, as necessary or desired, and as would be known and practiced by those of ordinary skill in the art. Exemplary supplements include, but are not limited to, chemical gene selection agents, hormones and other growth factors, (e.g., insulin, transferrin, epidermal growth factor, serum, somatotropin, pituitary extract, aprotinin); salts (e.g., calcium, magnesium and phosphate), and buffers (e.g., HEPES (4-[2-Hydroxyethyl]-1-piperazine-ethanesulfonic acid)); nucleosides and bases (e.g., adenosine, thymidine, hypoxanthine); protein and hydrolysates; antibiotics (e.g., gentamycin); cell protective agents (e.g., a Pluronic polyol (PLURONIC® F68)) and extracellular matrix proteins (e.g., fibronectin). Supplements that support the growth and maintenance of particular cell cultures are able to be readily determined by those of ordinary skill in the art, such as is described, for example, by Barnes et al. (Cell, 22:649 (1980)); in Mammalian Cell Culture, Mather, J. P., ed., Plenum Press, NY (1984); and in U.S. Pat. No. 5,721,121.

As used herein, the term "bioreactor" refers to any apparatus, closed container or vessel (e.g., a fermentation chamber) that is used for growing cell cultures. Bioreactors allow controlling various parameters during the cell culture process including, but not limited to, the circulation loop flow, pH, the temperature, the overpressure and/or the medium perfusion rate. Bioreactors include commercially available bioreactors, classical fermenters and cell culture perfusion systems, as well as disposable bioreactors.

The bioreactor can be of any size that is useful for culturing cells at a desirable scale in accordance with a method of the disclosure. For example, a bioreactor employed in the methods of the present disclosure may be at least about 0.1, 0.5, 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 340, 350, 360, 370, 380, 390, 400, 410, 420, 430, 440, 450, 460, 470, 480, 490, 500, 550, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 10,500, 11,000, 11,500, 12,0000, 13,000, 14,000, 15,000 liters or more, or any intermediate volume. In some embodiments, a bioreactor employed in the methods of the present disclosure may be used for large-scale production of a protein of interest. In such embodiments, a bioreactor employed in the methods of the present disclosure may be a 1,000 L bioreactor, a 2,500 L bioreactor, a 5,000 L bioreactor, a 8,000 L bioreactor, a 10,000 L bioreactor, a 12,000 L bioreactor, or a 15,000 L or larger bioreactor.

A suitable bioreactor may be composed of (i.e., constructed of) any material that is suitable for holding cell cultures under the culture conditions of the present disclosure and is conducive to cell growth and viability. For example, a bioreactor employed in the methods of the present disclosure can be made of glass, plastic or metal. However, the materials comprising the bioreactor should not interfere with expression or stability of the polypeptide product. Suitable bioreactors are known in the art and commercially available. In embodiments, the bioreactor is a N-1 seed bioreactor (N-1 bioreactor).

A perfusion bioreactor used in the methods of the present disclosure can be a disposable perfusion bioreactor or any other traditional perfusion bioreactors. The bioreactor may optionally be equipped with any internal or external cell retention devices, including, but not limited to, spin filters, tangential flow membrane filters, dynamic membranes, ultrasonic separators, gravity settlers, continuous centrifuge or acoustic cell retention device, microfiltration devices, ultrafiltration devices, etc.

In some embodiments, the perfusion bioreactors of the disclosure are bioreactors capable of obtaining a high cell density and high cell viability during the perfusion process. In certain embodiments, the perfusion bioreactors are N-1 bioreactors (or N-1 seed bioreactors).

A "biomass capacitance probe" refers to a probe that can measure viable cell density, among other capabilities. A biomass capacitance probe uses capacitance to measure the total viable cells in a culture. Viable cells act as capacitors in an alternating electric field. The biomass capacitance probe can measure the charge from these cells, and report it.

The cell cultures encompassed by the methods of the present disclosure may be grown at any temperature appropriate for the cell type and culture conditions. In one embodiment, it is desirable to use a temperature between about 30° C. and 38° C., to enhance protein production. In another embodiment, the temperature is at least about 25° C., 26° C., 27° C., 28° C., 29° C., 30° C., 31° C., 32° C., 33° C., 34° C., 35° C., 36° C., 37° C., 38° C., 39° C., 40° C., or 41° C. It may also be desirable to use different temperatures at different times during the culture.

Methods of the Disclosure

In embodiments, the disclosure is directed to the use of at least one host cell protein biomarker to assess disulfide bond reduction in compositions comprising a protein of interest. In some embodiments, the disclosure relates to methods of predicting the occurrence of disulfide bond reduction or low molecular weight protein species in compositions comprising a protein of interest, wherein the expression or activity level of at least one host cell protein is measured and provides a benchmark value associated with the occurrence of disulfide bond reduction or low molecular weight species of said protein of interest. In other embodiments, the disclosure relates to methods of producing a protein of interest, wherein host cells capable of producing the protein of interest are cultured, the expression or activity level of at least one host cell protein is measured, and downstream isolation of the protein of interest is informed by the host cell protein measurements.

Methods of Predicting the Occurrence of Disulfide Bond Reduction and Low Molecular Weight Protein Species In some embodiments, a method of predicting the occurrence of disulfide bond reduction comprises measuring the expression or activity level of at least one host cell protein, which is not said protein of interest, wherein a host cell protein expression or activity level above a benchmark value is associated with the occurrence of disulfide bond reduction of said protein of interest. In some embodiments, a method of predicting the occurrence of low molecular weight protein species comprises measuring the expression or activity level of at least one host cell protein, which is not said protein of interest, wherein a host cell protein expression or activity level above a benchmark value is associated with the occurrence of low molecular weight protein species of said protein of interest. In some embodiments, the occurrence of disulfide bond reduction or low molecular weight protein species can be detected by capillary electrophoresis.

In embodiments, a method of predicting the occurrence of disulfide bond reduction or the occurrence of low molecular weight protein species is performed on a composition comprising a protein of interest. In some embodiments, the host cell protein is a CHO cell protein. In some embodiments, the composition comprising the protein of interest is produced from a cell culture. In some embodiments, the cell culture comprises a host cell capable of producing the protein of interest. In some embodiments, the cell culture comprises host cells capable of producing said protein of interest. In some embodiments, the cell culture comprises mammalian cells, e.g., CHO cells.

In some embodiments, a method of predicting the occurrence of disulfide bond reduction or the occurrence of low molecular weight protein species comprises determining the expression level of at least one host cell protein. In some embodiments, the method comprises determining the expression level of at least two host cell proteins. In some embodiments, the method comprises determining the expression level of at least three host cell proteins. In some embodiments, the method comprises determining the expression level of at least four, at least five, at least six, at least seven, at least eight, at least nine, at least ten, at least 15, at least 20, at least 25, at least 30, at least 35, at least 40, at least 45, at least 50, at least 75, or at least 100 host cell proteins.

In some embodiments, a method of predicting the occurrence of disulfide bond reduction or the occurrence of low molecular weight protein species comprises determining the activity level of at least one host cell protein. In some embodiments, the method comprises determining the activity level of at least two host cell proteins. In some embodiments, the method comprises determining the activity level of at least three, at least four, at least five, at least six, at least seven, at least eight, at least nine, at least ten, at least 15, at least 20, at least 25, at least 30, at least 35, at least 40, at least 45, at least 50, at least 75, or at least 100 host cell proteins.

In some embodiments, a method of predicting the occurrence of disulfide bond reduction or the occurrence of low molecular weight protein species comprises determining the expression level of at least one host cell protein involved in the oxidative stress pathway, the heat shock protein pathway, and/or the hypoxia-induced stress pathway. In some embodiments, the method comprises determining the expression level of at least one host cell protein involved in the oxidative stress pathway. In some embodiments, the method comprises determining the expression level of at least one host cell protein involved in the heat shock protein stress pathway. In some embodiments, the method comprises determining the expression level of at least one host cell protein involved in the hypoxia-induced stress pathway.

In some embodiments, a method of predicting the occurrence of disulfide bond reduction or the occurrence of low molecular weight protein species comprises determining the expression level of at least one host cell protein selected from the group consisting of thioredoxin (TRX-like or TRX 1, cytoplasmic), thioredoxin reductase, peroxiredoxin (PRDX-1, PRDX-2, or PRDX-6-like), dihydrofolate reductase, glucose-6-phosphate dehydrogenase (G6PD), 6-phosphogluconate dehydrogenase (6PGD), and glyceraldehyde-3-phosphate dehydrogenase (GAPDH). In some embodiments, the method comprises determining the expression level of at least one host cell protein selected from the group consisting of thioredoxin, thioredoxin reductase, and GAPDH. In some embodiments, the method comprises determining the expression level of at least thioredoxin. In some embodiments, the method comprises determining the expression level of at least thioredoxin reductase. In some embodiments, the method comprises determining the expression level of at least GAPDH. In some embodiments, the method comprises determining the expression level of glutathione S-transferase (GST P1, GST omega-1-like isoform 3, GST Y1-like, GST A4-like, or GST alpha-3-like), malate dehydrogenase (MDH, cytoplasmic-like), L-lactate dehydrogenase (L-LDH A chain), 6-phosphogluconate dehydrogenase (6-PDG, decarboxylating-like), protein disulfide-isomerase (PDI, PDI A4, PDI A3, or PDI A6-like), superoxide dismutase (SOD [Cu—Zn]-like), D-3-phosphoglycerate dehydrogenase (d-3-PHGDH-like), isocitrate dehydrogenase (IDH [NADP] cytoplasmic-like), Myeloid Zinc Finger 1 (MZF-1), or apoptosis-inducing factor 1 (AIFM1, mitochondrial-like). In some embodiments, the expression level of a host cell protein is measured in a cell culture fluid (CCF). In other embodiments, the expression level of a host cell protein is measured intracellularly. In some embodiments, the intracellular expression level is measured in a cell culture lysate. In particular embodiments, the expression level is measured by western blot analysis.

These enzymes play a critical role in normal cell redox regulation; and their presence in the disulfide reduced sample might suggest increased levels of oxidative stress in the cell culture condition that demonstrated disulfide reduction.

In some embodiments, a method of predicting the occurrence of disulfide bond reduction or the occurrence of low molecular weight protein species comprises determining the activity level of at least one host cell protein involved in the oxidative stress pathway, the heat shock protein pathway, and/or the hypoxia-induced stress pathway. In some embodiments, a method of predicting the occurrence of disulfide bond reduction or the occurrence of low molecular weight protein species comprises determining the activity level of at least one host cell protein involved in the oxidative stress pathway. In some embodiments, a method of predicting the occurrence of disulfide bond reduction or the occurrence of low molecular weight protein species comprises determining the activity level of at least one host cell protein involved in the heat shock protein pathway. In some embodiments, a method of predicting the occurrence of disulfide bond reduction or the occurrence of low molecular weight protein species comprises determining the activity level of at least one host cell protein involved in the hypoxia-induced stress pathway.

In some embodiments, a method of predicting the occurrence of disulfide bond reduction or the occurrence of low molecular weight protein species comprises determining the activity level of at least one host cell protein selected from the group consisting of thioredoxin (TRX-like or TRX 1, cytoplasmic), thioredoxin reductase, peroxiredoxin (PRDX-1, PRDX-2, or PRDX-6-like), dihydrofolate reductase, glucose-6-phosphate dehydrogenase (G6PD), 6-phosphogluconate dehydrogenase (6PGD), and glyceraldehyde-3-phosphate dehydrogenase (GAPDH). In some embodiments, the method comprises determining the activity level of at least one host cell protein selected from the group consisting of thioredoxin, thioredoxin reductase, and GAPDH. In some embodiments, the method comprises determining the activity level of at least thioredoxin. In some embodiments, the method comprises determining the activity level of at least thioredoxin reductase. In some embodiments, the method comprises determining the activity level of at least GAPDH. In some embodiments, the method comprises determining the activity level of glutathione S-transferase (GST P1, GST omega-1-like isoform 3, GST Y1-like, GST A4-like, or GST alpha-3-like), malate dehydrogenase (MDH, cytoplasmic-like), L-lactate dehydrogenase (L-LDH A chain), 6-phosphogluconate dehydrogenase (6-PDG, decarboxylating-like), protein disulfide-isomerase (PDI, PDI A4, PDI A3, or PDI A6-like), superoxide dismutase (SOD [Cu—Zn]-like), D-3-phosphoglycerate dehydrogenase (d-3-PHGDH-like), isocitrate dehydrogenase (IDH [NADP] cytoplasmic-like), Myeloid Zinc Finger 1 (MZF-1), or apoptosis-inducing factor 1 (AIFM1, mitochondrial-like). In some embodiments, the activity level of a host cell protein is measured in a cell culture fluid (CCF). In other embodiments, the activity level of a host cell protein is measured intracellularly. In some embodiments, the intracellular activity level is measured in a cell culture lysate. In particular embodiments, the activity level is measured by an activity assay.

In some embodiments, a method of predicting the occurrence of disulfide bond reduction or the occurrence of low molecular weight protein species comprises determining the activity level of at least one host cell protein selected from glyceraldehyde-3-phosphate dehydrogenase (GAPDH), thioredoxin reductase or glucose-6-phosphate dehydrogenase (G6PD).

In some embodiments, thioredoxin reductase activity level is measured by thioredoxin reductase activity assay. In some embodiments, G6PD activity level is measured by G6PD activity assay. In some embodiments, GAPDH activity level is measured by GAPDH activity assay.

In some embodiments, a method of predicting the occurrence of disulfide bond reduction or the occurrence of low molecular weight protein species comprises determining the expression level of at least one host cell protein and the activity level of at least one host cell protein.

In certain embodiments, a method of predicting the occurrence of disulfide bond reduction or the occurrence of low molecular weight protein species comprises determining the expression level of thioredoxin, and the occurrence of disulfide bond reduction or low molecular weight protein species in a protein of interest is indicated by a thioredoxin relative band intensity of about 200%, as determined by western blot analysis.

In certain embodiments, a method of predicting the occurrence of disulfide bond reduction or the occurrence of low molecular weight protein species comprises determining the expression level of thioredoxin reductase, and the occurrence of disulfide bond reduction or low molecular weight protein species in a protein of interest is indicated by a thioredoxin reductase relative band intensity of about 160%, as determined by western blot analysis.

In certain embodiments, a method of predicting the occurrence of disulfide bond reduction or the occurrence of low molecular weight protein species comprises determining the expression level of GAPDH, and the occurrence of disulfide bond reduction or low molecular weight protein species in a protein of interest is indicated by a GAPDH relative band intensity of about 140%, as determined by western blot analysis.

In certain embodiments, a method of predicting the occurrence of disulfide bond reduction or the occurrence of low molecular weight protein species comprises determining the activity level of thioredoxin reductase, and the occurrence of disulfide bond reduction or low molecular weight protein species in a protein of interest is indicated by a relative TrxR activity (AU) of 1.0 after 60 minutes, as determined by thioredoxin reductase activity assay.

In certain embodiments, a method of predicting the occurrence of disulfide bond reduction or the occurrence of low molecular weight protein species comprises determining the activity level of G6PD, and the occurrence of disulfide bond reduction or low molecular weight protein species in a protein of interest is indicated by a normalized resorufin fluorescence (AU) of 3.0, as determined by G6PD activity assay.

In certain embodiments, a method of predicting the occurrence of disulfide bond reduction or the occurrence of low molecular weight protein species comprises determining the activity level of GAPDH, and the occurrence of disulfide bond reduction or low molecular weight protein species in a protein of interest is indicated by a decrease in normalized GAPDH activity as compared to the control, as determined by GAPDH activity assay.

Methods of Producing a Protein

In some embodiments, a method of producing a protein of interest comprises: culturing host cells capable of producing said protein of interest; measuring the expression level or activity level of at least one host cell protein, which is not said protein of interest; and isolating said protein of interest if either the host cell protein expression or activity level is below a benchmark value. In embodiments, an expression or activity level at or above the benchmark value indicates the occurrence of disulfide bond reduction or the presence of low molecular weight species of the protein of interest. In some embodiments, the host cell protein is a CHO cell protein.

In some embodiments, a method of producing a protein of interest comprises determining the expression level of at least one host cell protein. In some embodiments, the method comprises determining the expression level of at least two host cell proteins. In some embodiments, the method comprises determining the expression level of at least three host cell proteins. In some embodiments, the method comprises determining the expression level of at least four, at least five, at least six, at least seven, at least eight, at least nine, at least ten, at least 15, at least 20, at least 25, at least 30, at least 35, at least 40, at least 45, at least 50, at least 75, or at least 100 host cell proteins.

In some embodiments, a method of producing a protein of interest comprises determining the activity level of at least one host cell protein. In some embodiments, the method comprises determining the activity level of at least two host cell proteins. In some embodiments, the method comprises determining the activity level of at least three, at least four, at least five, at least six, at least seven, at least eight, at least nine, at least ten, at least 15, at least 20, at least 25, at least 30, at least 35, at least 40, at least 45, at least 50, at least 75, or at least 100 host cell proteins.

In some embodiments, a method of predicting the occurrence of disulfide bond reduction or the occurrence of low molecular weight protein species comprises determining the expression level of at least one host cell protein involved in the oxidative stress pathway, the heat shock protein pathway, and/or the hypoxia-inducible factor 1-alpha pathway. In some embodiments, the method comprises determining the expression level of at least one host cell protein involved in the oxidative stress pathway. In some embodiments, the method comprises determining the expression level of at least one host cell protein involved in the heat shock protein stress pathway. In some embodiments, the method comprises determining the expression level of at least one host cell protein involved in the hypoxiainduced stress pathway.

In some embodiments, a method of producing a protein of interest comprises determining the expression level of at least one host cell protein selected from the group consisting of thioredoxin (TRX-like or TRX 1, cytoplasmic), thioredoxin reductase, peroxiredoxin (PRDX-1, PRDX-2, or PRDX-6-like), dihydrofolate reductase, glucose-6-phosphate dehydrogenase (G6PD), 6-phosphogluconate dehydrogenase (6PGD), and glyceraldehyde-3-phosphate dehydrogenase (GAPDH). In some embodiments, the method comprises determining the expression level of at least one host cell protein selected from the group consisting of thioredoxin, thioredoxin reductase, and GAPDH. In some embodiments, the method comprises determining the expression level of at least thioredoxin. In some embodiments, the method comprises determining the expression level of at least thioredoxin reductase. In some embodiments, the method comprises determining the expression level of at least GAPDH. In some embodiments, the method comprises determining the expression level of glutathione S-transferase (GST P1, GST omega-1-like isoform 3, GST Y1-like, GST A4-like, or GST alpha-3-like), malate dehydrogenase (MDH, cytoplasmic-like), L-lactate dehydrogenase (L-LDH A chain), 6-phosphogluconate dehydrogenase (6-PDG, decarboxylating-like), protein disulfide-isomerase (PDI, PDI A4, PDI A3, or PDI A6-like), superoxide dismutase (SOD [Cu—Zn]-like), D-3-phosphoglycerate dehydrogenase (d-3-PHGDH-like), isocitrate dehydrogenase (IDH [NADP] cytoplasmic-like), Myeloid Zinc Finger 1 (MZF-1), or apoptosis-inducing factor 1 (AIFM1, mitochondrial-like).

In some embodiments, the expression level of a host cell protein is measured in a cell culture fluid (CCF). In other embodiments, the expression level of a host cell protein is measured intracellularly. In some embodiments, the intracellular expression level is measured in a cell culture lysate. In particular embodiments, the expression level is measured by western blot analysis and qPCR.

In some embodiments, a method of predicting the occurrence of disulfide bond reduction or the occurrence of low molecular weight protein species comprises determining the activity level of at least one host cell protein involved in the oxidative stress pathway, the heat shock protein pathway, and/or the hypoxiainduced stress pathway. In some embodiments, a method of predicting the occurrence of disulfide bond reduction or the occurrence of low molecular weight protein species comprises determining the activity level of at least one host cell protein involved in the oxidative stress pathway. In some embodiments, a method of predicting the occurrence of disulfide bond reduction or the occurrence of low molecular weight protein species comprises determining the activity level of at least one host cell protein involved in the heat shock protein pathway. In some embodiments, a method of predicting the occurrence of disulfide bond reduction or the occurrence of low molecular weight protein species comprises determining the activity level of at least one host cell protein involved in the hypoxia-induced stress pathway.

In some embodiments, a method of predicting the occurrence of disulfide bond reduction or the occurrence of low molecular weight protein species comprises determining the activity level of at least one host cell protein selected from the group consisting of thioredoxin (TRX-like or TRX 1, cytoplasmic), thioredoxin reductase, peroxiredoxin (PRDX-1, PRDX-2, or PRDX-6-like), dihydrofolate reductase, glucose-6-phosphate dehydrogenase (G6PD), 6-phosphogluconate dehydrogenase (6PGD), and glyceraldehyde-3-phosphate dehydrogenase (GAPDH). In some embodiments, the method comprises determining the activity level of at least one host cell protein selected from the group consisting of thioredoxin, thioredoxin reductase, and GAPDH. In some embodiments, the method comprises determining the activity level of at least thioredoxin. In some embodiments, the method comprises determining the activity level of at least thioredoxin reductase. In some embodiments, the method comprises determining the activity level of at least GAPDH. In some embodiments, the method comprises determining the activity level of glutathione S-transferase (GST P1, GST omega-1-like isoform 3, GST Y1-like, GST A4-like, or GST alpha-3-like), malate dehydrogenase (MDH, cytoplasmic-like), L-lactate dehydrogenase (L-LDH A chain), 6-phosphogluconate dehydrogenase (6-PDG, decarboxylating-like), protein disulfide-isomerase (PDI, PDI A4, PDI A3, or PDI A6-like), superoxide dismutase (SOD [Cu—Zn]-like), D-3-phosphoglycerate dehydrogenase (d-3-PHGDH-like), isocitrate dehydrogenase (IDH [NADP] cytoplasmic-like), Myeloid Zinc Finger 1 (MZF-1), or apoptosis-inducing factor 1 (AIFM1, mitochondrial-like). In some embodiments, the activity level of a host cell protein is measured in a cell culture fluid (CCF). In other embodiments, the activity level of a host cell protein is measured intracellularly. In some embodiments, the intracellular activity level is measured in a cell culture lysate. In particular embodiments, the activity level is measured by an activity assay.

In some embodiments, a method producing a protein of interest comprises determining the activity level of at least one host cell protein selected from glyceraldehyde-3-phosphate dehydrogenase (GAPDH), thioredoxin reductase or glucose-6-phosphate dehydrogenase (G6PD).

In some embodiments, thioredoxin reductase activity level is measured by thioredoxin reductase activity assay. In some embodiments, G6PD activity level is measured by G6PD activity assay. In some embodiments, GAPDH activity level is measured by GAPDH activity assay.

In some embodiments, a method of producing a protein of interest comprises determining the expression level of at least one host cell protein and the activity level of at least one host cell protein.

In certain embodiments, a method of producing a protein of interest comprises determining the expression level of thioredoxin, and the occurrence of disulfide bond reduction or low molecular weight protein species in a protein of interest is indicated by a thioredoxin relative band intensity of about 200%, as determined by western blot analysis.

In certain embodiments, a method of producing a protein of interest comprises determining the expression level of thioredoxin reductase, and the occurrence of disulfide bond reduction or low molecular weight protein species in a protein of interest is indicated by a thioredoxin reductase relative band intensity of about 160%, as determined by western blot analysis.

In certain embodiments, a method of producing a protein of interest comprises determining the expression level of GAPDH, and the occurrence of disulfide bond reduction low molecular weight protein species in a protein of interest is indicated by a GAPDH relative band intensity of about 140%, as determined by western blot analysis.

In certain embodiments, a method of producing a protein of interest comprises determining the activity level of thioredoxin reductase, and the occurrence of disulfide bond reduction or low molecular weight protein species in a protein of interest is indicated by a relative TrxR activity (AU) of 1.0 after 60 minutes, as determined by thioredoxin reductase activity assay.

In certain embodiments, a method of producing a protein of interest comprises determining the activity level of G6PD, and the occurrence of disulfide bond reduction or low molecular weight protein species in a protein of interest is indicated by a normalized resorufin fluorescence (AU) of 3.0, as determined by G6PD activity assay.

In certain embodiments, a method of producing a protein of interest comprises determining the activity level of GAPDH, and the occurrence of disulfide bond reduction or low molecular weight protein species in a protein of interest is indicated by a decrease in normalized GAPDH activity as compared to the control, as determined by GAPDH activity assay.

Polypeptides and Proteins of Interest

Any polypeptide or protein that is expressible in a host cell may be produced as a polypeptide or protein of interest in accordance with the present disclosure. The polypeptide may be expressed from a gene that is endogenous to the host cell, or from a gene that is introduced into the host cell through genetic engineering. The polypeptide may be one that occurs in nature, or may alternatively have a sequence that was engineered or selected by the hand of man. An engineered polypeptide may be assembled from other polypeptide segments that individually occur in nature, or may include one or more segments that are not naturally occurring.

Polypeptides that may desirably be expressed in accordance with the present disclosure will often be selected on the basis of an interesting biological or chemical activity. For example, the present disclosure may be employed to express any pharmaceutically or commercially relevant enzyme, receptor, antibody, hormone, regulatory factor, antigen, binding agent, etc.

Antibodies

Given the large number of antibodies currently in use or under investigation as pharmaceutical or other commercial agents, production of antibodies is of interest in accordance with the present disclosure. Antibodies are proteins that have the ability to specifically bind a particular antigen. Any antibody, or an antigen-binding fragment thereof, that can be expressed in a host cell may be used in accordance with the present disclosure. In some embodiments, the antibody to be expressed is a monoclonal antibody, or an antigen-binding fragment thereof. In certain embodiments, the antibody is a polyclonal antibody, or an antigen-binding fragment thereof.

In another embodiment, the antibody is a chimeric antibody. A chimeric antibody contains amino acid fragments that are derived from more than one organism. Chimeric antibody molecules can include, for example, an antigen binding domain from an antibody of a mouse, rat, or other species, with human constant regions. A variety of approaches for making chimeric antibodies have been described. See e.g., Morrison et al., *Proc. Natl. Acad. Sci. U.S.A.* 81, 6851 (1985); Takeda et al., *Nature* 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

In another embodiment, the antibody is human antibody derived, e.g., through the use of ribosome-display or phage-display libraries (see, e.g., Winter et al., U.S. Pat. No. 6,291,159 and Kawasaki, U.S. Pat. No. 5,658,754) or the use of xenographic species in which the native antibody genes are inactivated and functionally replaced with human antibody genes, while leaving intact the other components of the native immune system (see, e.g., Kucherlapati et al., U.S. Pat. No. 6,657,103).

Five human immunoglobulin classes are defined on the basis of their heavy chain composition, and are named IgG, IgM, IgA, IgE, and IgD. The IgG-class and IgA-class antibodies are further divided into subclasses, namely, IgG1, IgG2, IgG3, and IgG4, and IgA1 and IgA2. The heavy chains in IgG, IgA, and IgD antibodies have three constant region domains, that are designated CH1, CH2, and CH3, and the heavy chains in IgM and IgE antibodies have four constant region domains, CH1, CH2, CH3, and CH4.

In another embodiment, the antibody is a humanized antibody. A humanized antibody is a chimeric antibody wherein the large majority of the amino acid residues are derived from human antibodies, thus minimizing any potential immune reaction when delivered to a human subject. In humanized antibodies, amino acid residues in the complementarity determining regions are replaced, at least in part, with residues from a non-human species that confer a desired antigen specificity or affinity. Such altered immunoglobulin molecules can be made by any of several techniques known in the art, (e.g., Teng et al., *Proc. Natl. Acad. Sci. USA.*, 80, 7308-7312 (1983); Kozbor et al., *Immunology Today,* 4, 7279 (1983); Olsson et al., *Meth. Enzymol.,* 92, 3-16 (1982)), and are made according to the teachings of PCT Publication WO92/06193 or EP 0239400, all of which are incorporated herein by reference). Humanized antibodies can also be commercially produced. For further reference, see Jones et al., *Nature* 321:522-525 (1986); Riechmann et al., *Nature* 332:323-329 (1988); and Presta, *Curr. Op. Struct. Biol.* 2:593-596 (1992), all of which are incorporated herein by reference.

In still another embodiment, the monoclonal, polyclonal, chimeric, or humanized antibodies described above may contain amino acid residues that do not naturally occur in any antibody in any species in nature. These foreign residues can be utilized, for example, to confer novel or modified specificity, affinity or effector function on the monoclonal, chimeric or humanized antibody. In another embodiment, the antibodies described above may be conjugated to drugs for systemic pharmacotherapy, such as toxins, low-molecular-weight cytotoxic drugs, biological response modifiers, and radionuclides (see e.g., Kunz et al., Calicheamicin derivative-carrier conjugates, US20040082764 A1).

Cells

Any mammalian cell or cell type susceptible to cell culture, and to expression of polypeptides, may be utilized in accordance with the present disclosure. Non-limiting examples of mammalian cells that may be used in accordance with the present disclosure include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells±DHFR (CHO, Urlaub and Chasin, Proc. Natl. Acad. Sci. USA, 77:4216 (1980)); mouse sertoli cells (TM4, Mather, *Biol. Reprod.,* 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL5 1); TM cells (Mather et al., Annals N.Y. Acad. Sci., 383:44-68 (1982)); MRC 5 cells; FS4 cells; and a human hepatoma line (Hep G2). In a particular embodiment, the present disclosure is used in the culturing of and expression of polypeptides and proteins from CHO cell lines.

Additionally, any number of commercially and non-commercially available hybridoma cell lines that express polypeptides or proteins may be utilized in accordance with the present disclosure. One skilled in the art will appreciate that hybridoma cell lines might have different nutrition requirements and/or might require different culture conditions for optimal growth and polypeptide or protein expression, and will be able to modify conditions as needed.

As noted above, in many instances the cells will be selected or engineered to produce high levels of protein or polypeptide. Often, cells are genetically engineered to produce high levels of protein, for example by introduction of a gene encoding the protein or polypeptide of interest and/or by introduction of control elements that regulate expression of the gene (whether endogenous or introduced) encoding the polypeptide of interest.

Certain polypeptides may have detrimental effects on cell growth, cell viability or some other characteristic of the cells that ultimately limits production of the polypeptide or protein of interest in some way. Even amongst a population of cells of one particular type engineered to express a specific polypeptide, variability within the cellular population exists such that certain individual cells will grow better and/or produce more polypeptide of interest. In certain embodiments of the present disclosure, the cell line is empirically selected by the practitioner for robust growth under the particular conditions chosen for culturing the cells. In particular embodiments, individual cells engineered to express a particular polypeptide are chosen for large-scale production based on cell growth, final cell density, percent cell viability, titer of the expressed polypeptide or any combination of these or any other conditions deemed important by the practitioner.

Media and Culture Conditions

In some embodiments, a mammalian host cell is cultured under conditions that promote the production of the polypeptide of interest, any polypeptide disclosed herein. Basal cell culture medium formulations are well known in the art. To these basal culture medium formulations the skilled artisan will add components such as amino acids, salts, sugars, vitamins, hormones, growth factors, buffers, antibiotics, lipids, trace elements and the like, depending on the requirements of the host cells to be cultured. The culture medium may or may not contain serum and/or protein. Various tissue culture media, including serum-free and/or defined culture media, are commercially available for cell culture. Tissue culture media is defined, for purposes of the disclosure, as a media suitable for growth of animal cells, and, in some embodiments, mammalian cells, in in vitro cell culture. Typically, tissue culture media contains a buffer, salts, energy source, amino acids, vitamins and trace essential elements. Any media capable of supporting growth of the appropriate eukaryotic cell in culture can be used; the disclosure is broadly applicable to eukaryotic cells in culture, particularly mammalian cells, and the choice of media is not crucial to the disclosure. Tissue culture media suitable for use in the disclosure are commercially available from, e.g., ATCC (Manassas, Va.). For example, any one or combination of the following media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (available from JRH Biosciences, Lenexa, Kans., USA), among others, which can be obtained from the American Type Culture Collection or JRH Biosciences, as well as other vendors. When defined medium that is serum-free and/or peptone-free is used, the medium is usually highly enriched for amino acids and trace elements. See, for example, U.S. Pat. No. 5,122,469 to Mather et al. and U.S. Pat. No. 5,633,162 to Keen et al.

In certain embodiments, cells can be grown in serum-free, protein-free, growth factor-free, and/or peptone-free media. The term "serum-free" as applied to media includes any mammalian cell culture medium that does not contain serum, such as fetal bovine serum. The term "insulin-free" as applied to media includes any medium to which no exogenous insulin has been added. By exogenous is meant, in this context, other than that produced by the culturing of the cells themselves. The term "IGF-1-free" as applied to media includes any medium to which no exogenous Insulin-like growth factor-1 (IGF-1) or analog (such as, for example, LongR3, [Ala31], or [Leu24][Ala31] IGF-1 analogs available from GroPep Ltd. of Thebarton, South Australia) has been added. The term "growth-factor free" as applied to media includes any medium to which no exogenous growth factor (e.g., insulin, IGF-1) has been added. The term "protein-free" as applied to media includes medium free from exogenously added protein, such as, for example, transferrin and the protein growth factors IGF-1 and insulin. Protein-free media may or may not have peptones. The term "peptone-free" as applied to media includes any medium to which no exogenous protein hydrolysates have been added such as, for example, animal and/or plant protein hydrolysates. Eliminating peptone from media has the advantages of reducing lot to lot variability and enhancing processing such as filtration. Chemically defined media are media in which every component is defined and obtained from a pure source, in certain embodiments, a non-animal source. In certain embodiments, the media is chemically defined and fully serum and protein free.

In some embodiments, one of the many individualized media formulations that have been developed to maximize cell growth, cell viability, and/or recombinant polypeptide production in a particular cultured host cell is utilized. The methods described herein may be used in combination with commercially available cell culture media or with a cell culture medium that has been individually formulated for use with a particular cell line. For example, an enriched medium that could support increased polypeptide production may comprise a mixture of two or more commercial media, such as, for instance, DMEM and Ham's F1 2 media combined in ratios such as, for example, 1:1, 1:2, 1:3, 1:4, 1:5, 1:6, 1:7, 1:8, or even up to 1:15 or higher. Alternatively or in addition, a medium can be enriched by the addition of nutrients, such as amino acids or peptone, and/or a medium (or most of its components with the exceptions noted below) can be used at greater than its usual, recommended concentration, for example at 2×, 3×, 4×, 5×, 6×, 7×, 8×, or even higher concentrations. As used herein, "1×" means the standard concentration, "2×" means twice the standard concentration, etc. In any of these embodiments, medium components that can substantially affect osmolality, such as salts, cannot be increased in concentration so that the osmolality of the medium falls outside of an acceptable range. Thus, a medium may, for example, be 8× with respect to all components except salts, which can be present at only 1×. An enriched medium may be serum free and/or protein free. Further, a medium may be supplemented periodically during the time a culture is maintained to replenish medium components that can become depleted such as, for example, vitamins, amino acids, and metabolic precursors. As is known in the art, different media and temperatures may have somewhat different effects on different cell lines, and the same medium and temperature may not be suitable for all cell lines.

Suitable culture conditions for mammalian cells are known in the art. See e.g. Animal cell culture: A Practical Approach, D. Rickwood, ed., Oxford university press, New York (1992). Mammalian cells may be cultured in suspension or while attached to a solid substrate. Furthermore, mammalian cells may be cultured, for example, in fluidized bed bioreactors, hollow fiber bioreactors, roller bottles, shake flasks, or stirred tank bioreactors, with or without microcarriers, and operated in a batch, fed batch, continuous, semi-continuous, or perfusion mode.

Monitoring Culture Conditions

In certain embodiments of the present disclosure, the practitioner may find it beneficial or necessary to periodically monitor particular conditions of the growing cell culture. Monitoring cell culture conditions allows the practitioner to determine whether the cell culture is producing recombinant polypeptide or protein at suboptimal levels or whether the culture is about to enter into a suboptimal production phase. In order to monitor certain cell culture conditions, it will be necessary to remove small aliquots of the culture for analysis. One of ordinary skill in the art will understand that such removal may potentially introduce contamination into the cell culture, and will take appropriate care to minimize the risk of such contamination.

As non-limiting example, it may be beneficial or necessary to monitor temperature, pH, cell density, viable cell density, cell viability, integrated viable cell density, lactate levels, ammonium levels, osmolality, amount of dissolved oxygen, $pCO_2$ levels, glutamine levels, glutamate levels, or glucose levels of the cell culture, or the titer of the expressed polypeptide or protein. In some embodiments, the expression or activity level of a host cell protein is monitored as an alternative or in addition to the above cell culture parameters. In some embodiments, such parameters are measured on a periodic basis. In particular embodiments, such parameters are measured on a daily basis. In some embodiments, such measurements are taken during growth phase of the cell culture. In some embodiments, such measurements are taken during the transition phase of the cell culture. In some embodiments, such measurements are taken during the production phase of the cell culture. In particular embodiments, the expression or activity level of a host cell protein is measured on day 1, 2, 3, 4, 5, 6, 7, 8, 9, 10, 11, 12, 13, 14, 15, 16, 17, 18, 19, 20, or 21 following the start of cell culture.

Numerous techniques are well known in the art that will allow one of ordinary skill in the art to measure these conditions. For example, cell density may be measured using a hemacytometer, a Coulter counter, or Cell density examination (CEDEX). Viable cell density may be determined by staining a culture sample with Trypan blue. Since only dead cells take up the Trypan blue, viable cell density can be determined by counting the total number of cells, dividing the number of cells that take up the dye by the total number of cells, and taking the reciprocal. Cell viability can also be measured using a biomass capacitance probe. HPLC can be used to determine the levels of lactate, ammonium or the expressed polypeptide or protein. Alternatively, the level of the expressed polypeptide or protein can be determined by standard molecular biology techniques such as coomassie staining of SDS-PAGE gels, Western blotting, Bradford assays, Lowry assays, Biuret assays, and UV absorbance. It may also be beneficial or necessary to monitor the post-translational modifications of the expressed polypeptide or protein, including phosphorylation and glycosylation.

Providing a Mammalian Cell Culture

Various methods of preparing mammalian cells for production of proteins or polypeptides by batch and fed-batch culture are well known in the art. A nucleic acid sufficient to achieve expression (typically a vector containing the gene encoding the polypeptide or protein of interest and any operably linked genetic control elements) may be introduced into the host cell line by any number of well-known techniques. Typically, cells are screened to determine which of the host cells have actually taken up the vector and express the polypeptide or protein of interest. Traditional methods of detecting a particular polypeptide or protein of interest expressed by mammalian cells include but are not limited to immunohistochemistry, immunoprecipitation, flow cytometry, immunofluorescence microscopy, SDS-PAGE, Western blots, enzyme-linked immunosorbentassay (ELISA), high performance liquid chromatography (HPLC) techniques, biological activity assays and affinity chromatography. One of ordinary skill in the art will be aware of other appropriate techniques for detecting expressed polypeptides or proteins. If multiple host cells express the polypeptide or protein of interest, some or all of the listed techniques can be used to determine which of the cells expresses that polypeptide or protein at the highest levels.

Once a cell that expresses the polypeptide or protein of interest has been identified, the cell is propagated in culture by any of the variety of methods well-known to one of ordinary skill in the art. The cell expressing the polypeptide or protein of interest is typically propagated by growing it at a temperature and in a medium that is conducive to the survival, growth and viability of the cell. The initial culture volume can be of any size, but is often smaller than the culture volume of the production bioreactor used in the final production of the polypeptide or protein of interest, and frequently cells are passaged several times in bioreactors of increasing volume prior to seeding the production bioreactor. The cell culture can be agitated or shaken to increase oxygenation of the medium and dispersion of nutrients to the cells. Alternatively or additionally, special sparging devices that are well known in the art can be used to increase and control oxygenation of the culture. In accordance with the present invention, one of ordinary skill in the art will understand that it can be beneficial to control or regulate certain internal conditions of the bioreactor, including but not limited to pH, temperature, oxygenation, etc.

The starting cell density in the production bioreactor can be chosen by one of ordinary skill in the art. In accordance with the present disclosure, the starting cell density in the production bioreactor can be as low as a single cell per culture volume. In preferred embodiments of the present disclosure, starting cell densities in the production bioreactor can range from about $2\times10^2$ viable cells per mL to about $2\times10^3$, $2\times10^4$, $2\times10^5$, $2\times10^6$, $5\times10^6$ or $10\times10^6$ viable cells per mL and higher.

Initial and intermediate cell cultures may be grown to any desired density before seeding the next intermediate or final production bioreactor. It is preferred that most of the cells remain alive prior to seeding, although total or near total viability is not required. In one embodiment of the present disclosure, the cells may be removed from the supernatant, for example, by low-speed centrifugation. It may also be desirable to wash the removed cells with a medium before seeding the next bioreactor to remove any unwanted metabolic waste products or medium components. The medium may be the medium in which the cells were previously grown or it may be a different medium or a washing solution selected by the practitioner of the present disclosure.

The cells may then be diluted to an appropriate density for seeding the production bioreactor. In a preferred embodiment of the present disclosure, the cells are diluted into the same medium that will be used in the production bioreactor. Alternatively, the cells can be diluted into another medium or solution, depending on the needs and desires of the practitioner of the present disclosure or to accommodate particular requirements of the cells themselves, for example, if they are to be stored for a short period of time prior to seeding the production bioreactor.

Initial Growth Phase

Once the production bioreactor has been seeded as described above, the cell culture is maintained in the initial growth phase under conditions conducive to the survival, growth and viability of the cell culture. The precise conditions will vary depending on the cell type, the organism from which the cell was derived, and the nature and character of the expressed polypeptide or protein.

In accordance with the present disclosure, the production bioreactor can be any volume that is appropriate for large-scale production of polypeptides or proteins. In a preferred embodiment, the volume of the production bioreactor is at least 500 liters. In other preferred embodiments, the volume of the production bioreactor is 1000, 2500, 5000, 8000, 10,000, 12,000 liters or more, or any volume in between. One of ordinary skill in the art will be aware of and will be able to choose a suitable bioreactor for use in practicing the present disclosure. The production bioreactor may be constructed of any material that is conducive to cell growth and viability that does not interfere with expression or stability of the produced polypeptide or protein.

The temperature of the cell culture in the initial growth phase will be selected based primarily on the range of temperatures at which the cell culture remains viable. For example, during the initial growth phase, CHO cells grow well at 37° C. In general, most mammalian cells grow well within a range of about 25° C. to 42° C. Preferably, mammalian cells grow well within the range of about 35° C. to 40° C. Those of ordinary skill in the art will be able to select appropriate temperature or temperatures in which to grow cells, depending on the needs of the cells and the production requirements of the practitioner.

In one embodiment of the present disclosure, the temperature of the initial growth phase is maintained at a single, constant temperature. In another embodiment, the temperature of the initial growth phase is maintained within a range of temperatures. For example, the temperature may be steadily increased or decreased during the initial growth phase. Alternatively, the temperature may be increased or decreased by discrete amounts at various times during the initial growth phase. One of ordinary skill in the art will be able to determine whether a single or multiple temperatures should be used, and whether the temperature should be adjusted steadily or by discrete amounts.

The cells may be grown during the initial growth phase for a greater or lesser amount of time, depending on the needs of the practitioner and the requirement of the cells themselves. In one embodiment, the cells are grown for a period of time sufficient to achieve a viable cell density that is a given percentage of the maximal viable cell density that the cells would eventually reach if allowed to grow undisturbed. For example, the cells may be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal viable cell density.

In another embodiment the cells are allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days. In some cases, the cells may be allowed to grow for a month or more. The cells would be grown for 0 days in the production bioreactor if their growth in a seed bioreactor, at the initial growth phase temperature, was sufficient that the viable cell density in the production bioreactor at the time of its inoculation is already at the desired percentage of the maximal viable cell density. The practitioner of the present disclosure will be able to choose the duration of the initial growth phase depending on polypeptide or protein production requirements and the needs of the cells themselves.

The cell culture may be agitated or shaken during the initial culture phase in order to increase oxygenation and dispersion of nutrients to the cells. In accordance with the present disclosure, one of ordinary skill in the art will understand that it can be beneficial to control or regulate certain internal conditions of the bioreactor during the initial growth phase, including but not limited to pH, temperature, oxygenation, etc. For example, pH can be controlled by supplying an appropriate amount of acid or base and oxygenation can be controlled with sparging devices that are well known in the art.

Shifting Culture Conditions

In accordance with the teaching of the present disclosure, at the end of the initial growth phase, at least one of the culture conditions may be shifted so that a second set of culture conditions is applied and a metabolic shift occurs in the culture. The accumulation of inhibitory metabolites, most notably lactate and ammonia, inhibits growth. A metabolic shift, accomplished by, e.g., a change in the temperature, pH, osmolality or chemical inductant level of the cell culture, may be characterized by a reduction in the ratio of a specific lactate production rate to a specific glucose consumption rate. In one non-limiting embodiment, the culture conditions are shifted by shifting the temperature of the culture. However, as is known in the art, shifting temperature is not the only mechanism through which an appropriate metabolic shift can be achieved. For example, such a metabolic shift can also be achieved by shifting other culture conditions including, but not limited to, pH, osmolality, and sodium butyrate levels. As discussed above, the timing of the culture shift will be determined by the practitioner of the present disclosure, based on polypeptide or protein production requirements or the needs of the cells themselves.

When shifting the temperature of the culture, the temperature shift may be relatively gradual. For example, it may take several hours or days to complete the temperature change. Alternatively, the temperature shift may be relatively abrupt. For example, the temperature change may be complete in less than several hours. Given the appropriate production and control equipment, such as is standard in the commercial large-scale production of polypeptides or proteins, the temperature change may even be complete within less than an hour.

The temperature of the cell culture in the subsequent growth phase will be selected based primarily on the range of temperatures at which the cell culture remains viable and expresses recombinant polypeptides or proteins at commercially adequate levels. In general, most mammalian cells remain viable and express recombinant polypeptides or proteins at commercially adequate levels within a range of about 25° C. to 42° C. Preferably, mammalian cells remain viable and express recombinant polypeptides or proteins at commercially adequate levels within a range of about 25° C. to 35° C. Those of ordinary skill in the art will be able to select appropriate temperature or temperatures in which to grow cells, depending on the needs of the cells and the production requirements of the practitioner.

In one embodiment of the present disclosure, the temperature of the subsequent growth phase is maintained at a single, constant temperature. In another embodiment, the temperature of the subsequent growth phase is maintained within a range of temperatures. For example, the temperature may be steadily increased or decreased during the subsequent growth phase. Alternatively, the temperature may be increased or decreased by discrete amounts at various times during the subsequent growth phase. One of ordinary skill in the art will understand that multiple discrete temperature shifts are encompassed in this embodiment. For example, the temperature may be shifted once, the cells maintained at this temperature or temperature range for a certain period of time, after which the temperature may be shifted again—either to a higher or lower temperature. The temperature of the culture after each discrete shift may be constant or may be maintained within a certain range of temperatures.

Subsequent Production Phase

In accordance with the present disclosure, once the conditions of the cell culture have been shifted as discussed above, the cell culture is maintained for a subsequent production phase under a second set of culture conditions conducive to the survival and viability of the cell culture and appropriate for expression of the desired polypeptide or protein at commercially adequate levels.

As discussed above, the culture may be shifted by shifting one or more of a number of culture conditions including, but not limited to, temperature, pH, osmolality, and sodium butyrate levels. In one embodiment, the temperature of the culture is shifted. According to this embodiment, during the subsequent production phase, the culture is maintained at a temperature or temperature range that is lower than the temperature or temperature range of the initial growth phase. For example, during the subsequent production phase, CHO cells express recombinant polypeptides and proteins well within a range of 25° C. to 35° C. As discussed above, multiple discrete temperature shifts may be employed to increase cell density or viability or to increase expression of the recombinant polypeptide or protein.

In accordance with the present disclosure, the cells may be maintained in the subsequent production phase until a desired cell density or production titer is reached. In one embodiment, the cells are maintained in the subsequent production phase until the titer to the recombinant polypeptide or protein reaches a maximum. In other embodiments, the culture may be harvested prior to this point, depending on the production requirement of the practitioner or the needs of the cells themselves. For example, the cells may be maintained for a period of time sufficient to achieve a viable cell density of 1, 5, 10, 15, 20, 25, 30, 35, 40, 45, 50, 55, 60, 65, 70, 75, 80, 85, 90, 95 or 99 percent of maximal viable cell density. In some cases, it may be desirable to allow the viable cell density to reach a maximum, and then allow the viable cell density to decline to some level before harvesting the culture. In an extreme example, it may be desirable to allow the viable cell density to approach or reach zero before harvesting the culture.

In another embodiment of the present disclosure, the cells are allowed to grow for a defined period of time during the subsequent production phase. For example, depending on the concentration of the cell culture at the start of the subsequent growth phase, the temperature at which the cells are grown, and the intrinsic growth rate of the cells, the cells may be grown for 1, 2, 3, 4, 5, 6, 7, 8, 9, 10, 11, 12, 13, 14, 15, 16, 17, 18, 19, 20 or more days. In some cases, the cells may be allowed to grow for a month or more. The practitioner of the present invention will be able to choose the duration of the subsequent production phase depending on polypeptide or protein production requirements and the needs of the cells themselves.

In certain cases, it may be beneficial or necessary to supplement the cell culture during the subsequent production phase with nutrients or other medium components that have been depleted or metabolized by the cells. For example, it might be advantageous to supplement the cell culture with nutrients or other medium components observed to have been depleted during monitoring of the cell culture. Alternatively or additionally, it may be beneficial or necessary to supplement the cell culture prior to the subsequent production phase. As non-limiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source.

These supplementary components may all be added to the cell culture at one time, or they may be provided to the cell culture in a series of additions. In one embodiment of the present disclosure, the supplementary components are provided to the cell culture at multiple times in proportional amounts. In another embodiment, it may be desirable to provide only certain of the supplementary components initially, and provide the remaining components at a later time. In yet another embodiment of the present disclosure, the cell culture is fed continually with these supplementary components.

In accordance with the present disclosure, the total volume added to the cell culture should optimally be kept to a minimal amount. For example, the total volume of the medium or solution containing the supplementary components added to the cell culture may be 1, 2, 3, 4, 5, 6, 7, 8, 9, 10, 15, 20, 25, 30, 35, 40, 45 or 50% of the volume of the cell culture prior to providing the supplementary components.

The cell culture may be agitated or shaken during the subsequent production phase in order to increase oxygenation and dispersion of nutrients to the cells. In accordance with the present invention, one of ordinary skill in the art will understand that it can be beneficial to control or regulate certain internal conditions of the bioreactor during the subsequent growth phase, including but not limited to pH, temperature, oxygenation, etc. For example, pH can be controlled by supplying an appropriate amount of acid or base and oxygenation can be controlled with sparging devices that are well known in the art.

Isolation of Expressed Polypeptide or Protein of Interest

In general, it will typically be desirable to isolate and/or purify proteins or polypeptides of interest expressed according to the present disclosure. In a preferred embodiment, the expressed polypeptide or protein is secreted into the medium and thus cells and other solids may be removed, as by centrifugation or filtering for example, as a first step in the purification process.

Alternatively, the expressed polypeptide or protein is bound to the surface of the host cell. In this embodiment, the media is removed and the host cells expressing the polypeptide or protein are lysed as a first step in the purification process. Lysis of mammalian host cells can be achieved by any number of means well known to those of ordinary skill in the art, including physical disruption by glass beads and exposure to high pH conditions.

The polypeptide or protein may be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference). For immunoaffinity chromatography in particular, the protein may be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the polypeptide or protein during the purification process. Protease inhibitors are particularly desired when cells must be lysed in order to isolate and purify the expressed polypeptide or protein. One of ordinary skill in the art will appreciate that the exact purification technique will vary depending on the character of the polypeptide or protein to be purified, the character of the cells from which the polypeptide or protein is expressed, and the composition of the medium in which the cells were grown.

EXAMPLES

Example 1

Cell Culture Conditions and Preparation of Samples for Analysis

A proprietary cell culture medium and two proprietary recombinant CHO cell lines expressing different IgG antibodies were used for the experiments described in the following Examples. The cell culture medium was chemically defined and fully serum free. Recombinant IgG producing CHO cells were maintained in suspension culture in 250-mL, 1-L and 3-L shake flasks, and a $CO_2$ shaker incubator (Kuhner) was used for incubation at 36.5° C., 150 rpm, at a $CO_2$ concentration of 5%.

Lab scale reactor cultivations for both N−1 seed and Fed-batch production were carried out in 5-L stirred tank reactors (Sartorius). All the 5-L reactors were equipped with two 45° pitched tri-blade impellers, pH and DO probe. In the N−1 seed, cultivations were inoculated from 3-L shake flask cultures in the range of $0.4$–$0.8 \times 10^6$ cells/mL and at a temperature of 36.5° C. The initial working volume of the 5-L bioreactor was at 3 L. pH was controlled in the range of 7.0 to 7.4 by 1M sodium carbonate addition and $CO_2$ gas sparging. Impeller agitation was set at 260 rpm, and aeration was provided by pure oxygen sparging through 0.5 mm drilled hole spargers. Dissolved oxygen was maintained at a level of 50% via cascade oxygen sparging. Antifoam (EX-CELL antifoam, Sigma-Aldrich) was added to the bioreactor to control foam levels. Cell density was measured by daily offline measurements (Vi-cell, Beckman Coulter) and/or via online capacitance probes (Hamilton). Daily offline samples were also monitored for pH, dissolved oxygen, and $pCO_2$ via phOX instruments (Nova Biomedical), and glucose and lactate profiles were measured with Cedex Bio HT (Roche).

Cell culture fluid (CCF) harvests were carried out with depth filtration using 10SP02A and 90ZB05A as primary and secondary depth filters, respectively. During filtration, differential pressures were monitored as a function of loading, and filter resistance was calculated as the ratio of differential pressure to filtration flux. Filtration experiments were performed using a PendoTECH instrument (PendoTECH, Princeton, N.J.) controlled by NFF SS software. Unless noted, equilibration of the filter was performed using reverse osmosis de-ionized water (RODI) at 600 liters per square meter per hour (LMH) until reaching >100 $L/m^2$, followed by loading at a constant flux of 50 LMH, based upon primary depth effective filtration area (EFA), followed by a PBS chase at 15 $L/m^2$. Harvested cell culture fluid was stored either at −80° C., or 4° C. for up to three days prior to commencing experimental testing.

Samples from lab and manufacturing scale bioreactors were purified with affinity chromatography (Mab Select PCC resin, GE Healthcare Life Sciences, Marlborough, Mass., USA) in a batch binding, 96-well format using centrifugation of effluent through 25-30 µm filter plates. Plates were prepared with resin by adding 300 µL of slurried resin into 96-well filter plates, centrifuging at 2000 rpm for 1 minute, and discarding flowthrough from the 96 well waste collection plate. Plates were then equilibrated with 300 µl 1× phosphate buffered saline (Thermo Scientific, Bremen, Del.), and centrifuged as above in triplicate. Filtered HCCF samples were adjusted to ≤2 mg/ml, and 200 µl was loaded onto prepared plates in duplicate, and centrifuged at 2000 rpm for 1 minute, discarding flowthrough. This was repeated a total of four times. Wells were then washed two times with 1× PBS as indicated in the equilibration step above, followed by two washes with either succinate or acetate buffer pH 5.5-5.8, and processed as above. A fresh waste collection plate used to elute samples, and samples were eluted by adding 196 µl of succinate or acetate elution buffer (pH 3.0-3.8) to the resin, and centrifuging at 2000 rpm for 1 minute. Elution step was repeated twice for a total of three elutions per well. Protein concentration was determined using the appropriate extinction coefficient using a Lunatic UV/Vis reader (Unchained Labs, Pleasanton, Calif., USA).

For HCCF samples IgG-depleted for proteomics for proteomics analysis, plates were loaded with resin and equilibrated as indicated above. HCCF was added into wells in quadruplicate, agitated to resuspend resin slurry, incubated for 1 hour, then centrifuged at 2000 rpm for 1 minute into a collection plate. IgG-depleted HCCF from each sample was pooled and concentrated to >25 mg/ml using Amicon Ultra-15 Centrifugal Filter Units (Millipore Sigma, St. Louis, Mo., USA) and adjusted to a final concentration of 20 mg/ml total protein with 2 mg/ml BSA (Millipore Sigma, St. Louis, Mo., USA) to be used for signal normalization.

Example 2

Comparison of Bioreactor Performance Across LMW-Forming and Non-Forming Batches

In order to assess reduction risk for a monoclonal antibody (mAb A), HCCF aliquots from batches produced during two separate manufacturing campaigns were held under low dissolved oxygen conditions overnight, purified by protein A and screened for the presence of disulfide reduction by capillary electrophoresis (results summarized in Table 1). Out of eleven lots tested, reduced mAb species were detected in the protein A eluate of nine batches, with only two batches (C1L2 and C2L2) showing no reduction.

TABLE 1

Summary of mAb A Disulfide Reduction From Manufacturing Campaign Batches

| Batch Name | Monomer % | LMW[1] % | Product Pool |
|---|---|---|---|
| C1L1 | 96.7 | 3.3 | Drug Substance |
| C1L2 | 98.9 | 1.1 | Protein A Eluate |
| C1L4 | 96.7 | 3.3 | Protein A Eluate |
| C1L5 | 63.9 | 36.1 | Protein A Eluate |
| C1L6 | 7.9 | 92.1 | Protein A Eluate |
| C1L7 | 13.7 | 86.3 | Protein A Eluate |
| C2L1 | 69.9 | 30.1 | Protein A Eluate |
| C2L2 | 99.2 | 0.8 | Protein A Eluate |
| C2L3 | 30.0 | 70.0 | Protein A Eluate |
| C2L6 | 1.7 | 98.3 | Protein A Eluate |
| C2L7 | 7.4 | 92.6 | Protein A Eluate |

Figure 1C:
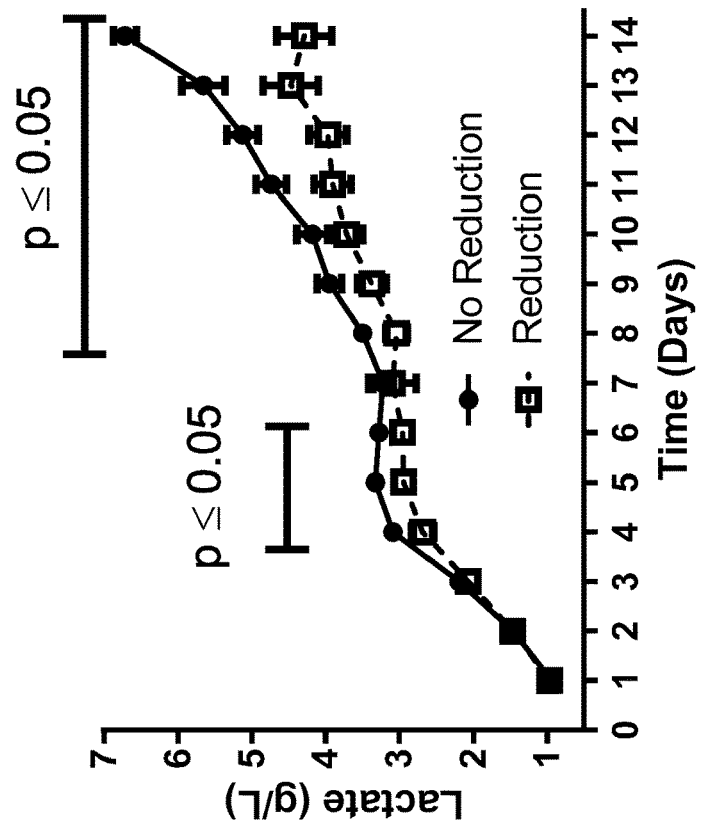
Figure 1E:
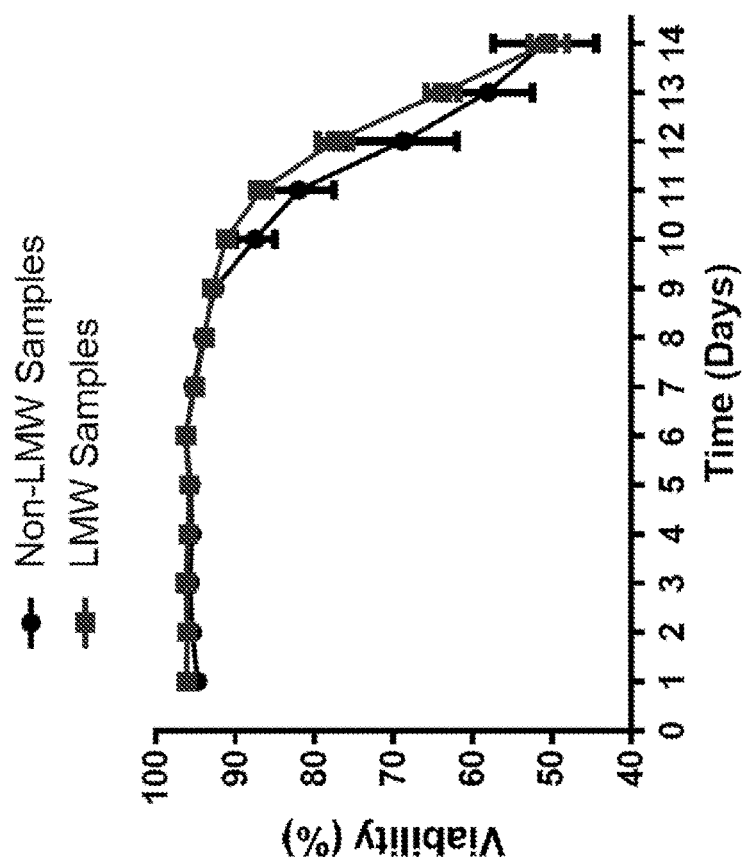
Figure 1F:
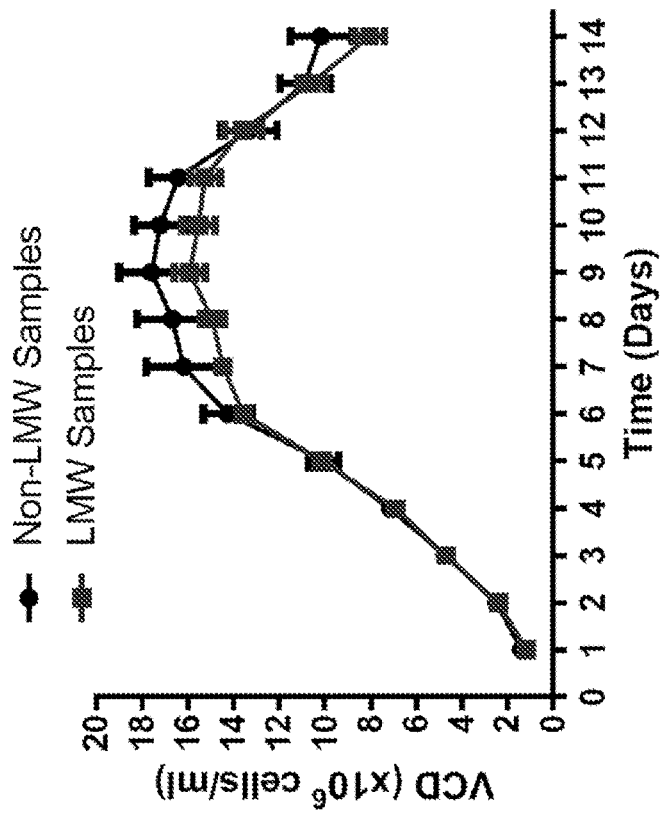
Figure 1H:
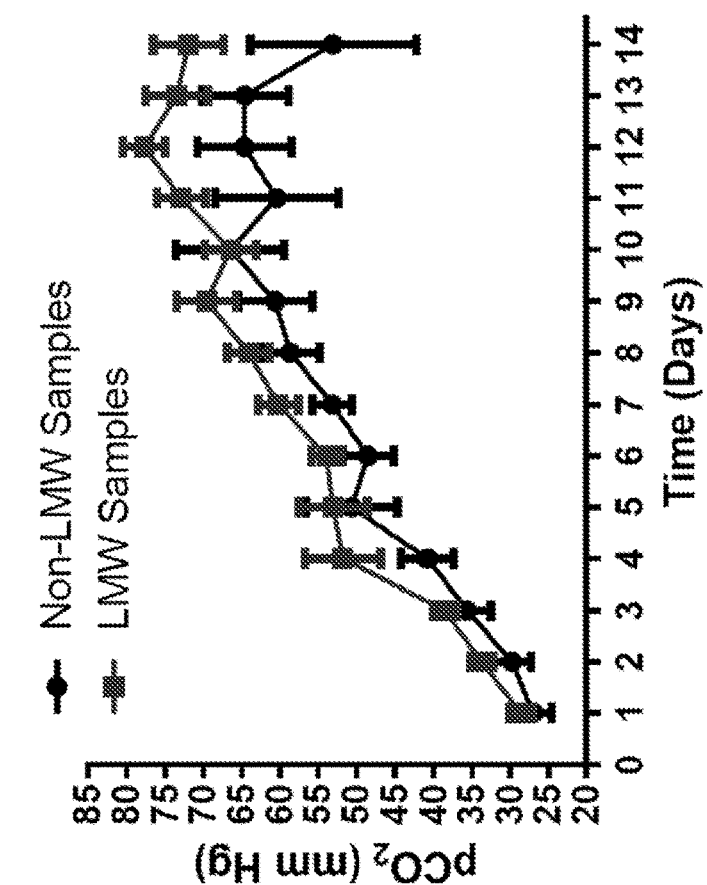
Figure 1G:
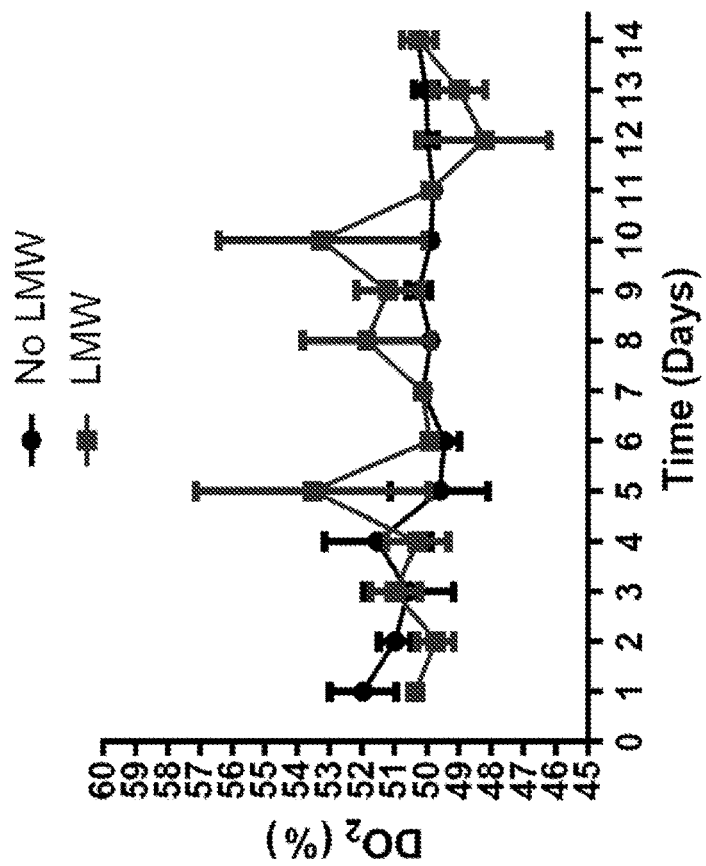
Figures 1I, 1J:
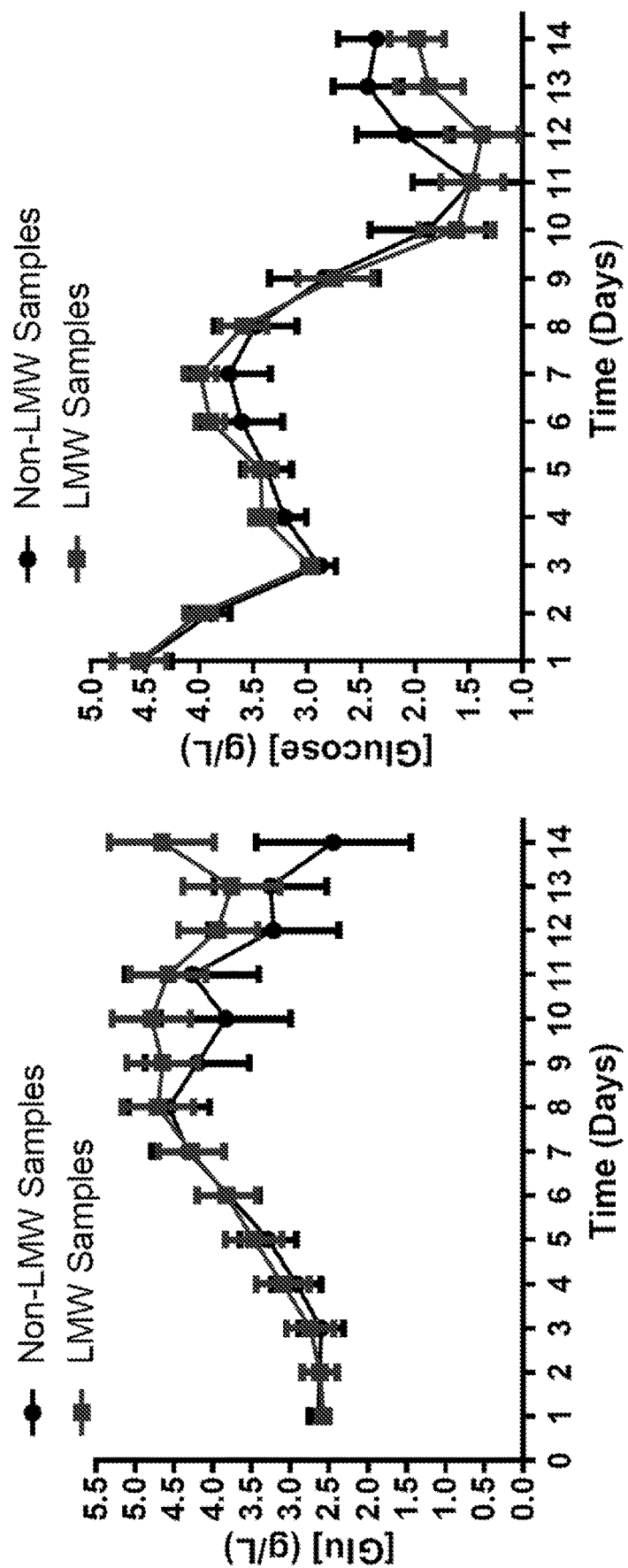

To better visualize bioreactor profiles associated with disulfide bond reduction, data was compiled for samples showing reduction and those that did not. FIGS. 1A-1J show twelve upstream parameters in antibody manufacturing scale and lab-scale runs plotted against time. Data from samples±disulfide bond reduction were averaged across 8 separate lab-, pilot-, and manufacturing scale batches for each condition. For samples demonstrating disulfide bond reduction of the tested antibody, bioreactor pH showed a statistically significant 0.05 pH unit lower trend starting at day 7 (FIG. 1A). Glutamine consumption decreased approximately 2-fold starting at day 9 (FIG. 1B), and ammonium production trended higher in the disulfide reduced samples and was 2.2-fold higher on day 14 than in non-reduced samples (FIG. 1D). Surprisingly, lactate production trended lower starting at day 8 in disulfide reduced samples, with day 14 lactate in the CCF approximately 1.5-fold lower than the non-reduced samples (FIG. 1C). Other measured parameters (FIGS. 1E-1J), such as peak viable cell density and percent cell viability, showed no correlation with LMW formation despite being direct factors in the amount of cytosol release into CCF. Accordingly, these data indicate that standard measures of bioreactor performance or bioreactor metabolite levels do not reliably identify or predict disulfide bond reduction.

Example 3

Proteomics Analysis of HCCF in Disulfide Reduced and Non-Reduced Samples

To better characterize cell culture conditions that may influence disulfide bond reduction potential in harvested cell culture fluid (HCCF), two cultures were harvested at separate points to compare normal (NC D14) and low viability (LVC D15) conditions associated with production of a monoclonal antibody. Disulfide bond reduction was evaluated under multiple storage conditions by capillary electrophoresis. Briefly, HCCF from laboratory-scale, pilot-scale, and/or clinical manufacturing-scale cultures was warmed to room temperature, sterile filtered in a biosafety cabinet, and split into sterile single use media bottle assemblies equipped with luer lock sterile air filters. Samples to be tested for disulfide bond reduction were sparged with nitrogen for 30-60 minutes to remove dissolved oxygen, after which bottle inlets and outlets were sealed. Samples were stored at either 2-8° C. or room temperature for 24 hours with or without air overlay, then treated with 20 mM iodoacetamide (Sigma) prior to protein A purification. The extent of disulfide bond reduction was measured by capillary electrophoresis using a Caliper LabChip GXII system (Perkin Elmer) and analyzed using LabChip GX software. The cell viability conditions are shown in Table 2.

TABLE 2

Cell Viability Conditions for Two mAb A Lab Scale Bioreactor Runs

| Process Condition | Culture Harvest Day | Normalized Peak Viable Cell Density ($\times 10^6$ cells/ml) | Normalized Viable Cell Density (Harvest)[1] ($\times 10^6$ cells/ml) | Cell Viability[2] (%) |
|---|---|---|---|---|
| Normal Condition (NC) | 14 | 1 | 0.44 | <45 |
| Low Viability Condition (LVC) | 15 | 1 | 0.19 | <22 |

Figure 2A:
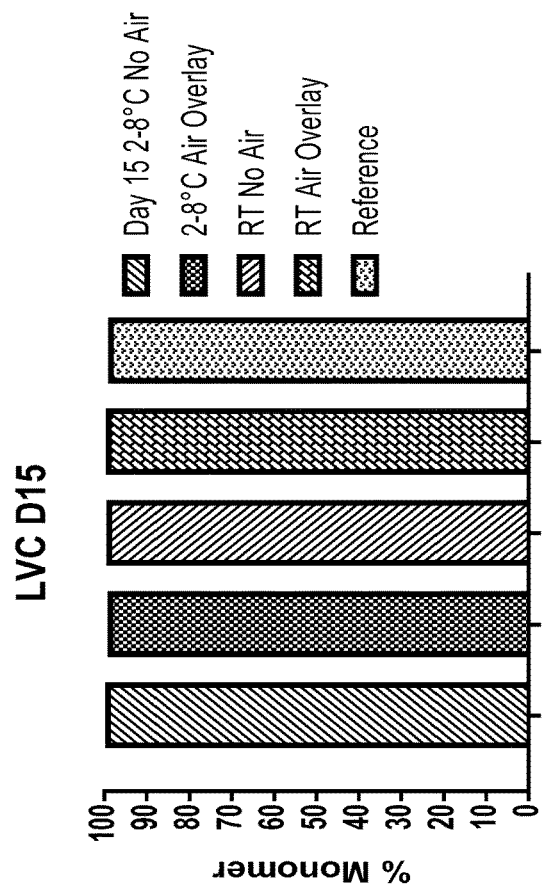
FIGS. 2A and 2B show the extent of disulfide bond reduction in samples obtained from normal (NC D14) and low viability (LVC D15) cell culture conditions associated with production of a monoclonal antibody. Measurements of the peak viable cell density (VCD), VCD, and % viability of cells are also indicated for each cell culture condition. In particular.
Figure 2B:
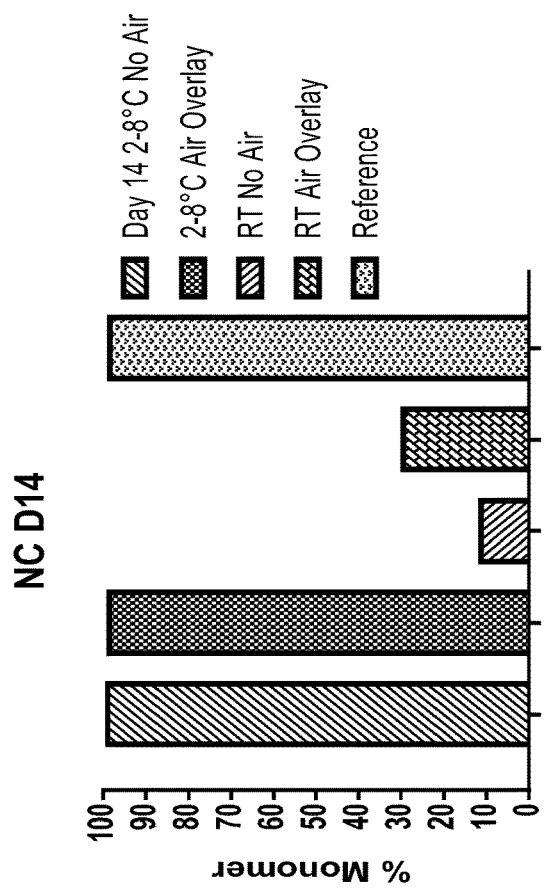

[1]Measured on terminal day of culture (pre-harvest)
[2]Calculated as ratio of harvest day viable cell density to peak viable cell density The results of these experiments are shown in FIGS. 2A and 2B. Surprisingly, the condition with normal viability (NC D14) showed significant disulfide bond reduction when stored at room temperature, with only 11.2% intact monomer after storage under low $DO_2$, and 29.5% monomer when stored under air (FIG. 2A). In contrast, the low viability condition (LVC D15) showed no significant disulfide bond reduction, even under low $DO_2$ conditions at room temperature (FIG. 2B). These data confirm that parameters such as peak variable cell density and harvest viability do not directly predict disulfide formation.

To better understand the differences in protein content in the HCCF, samples from each bioreactor (NC D14, LVC D15) were IgG-depleted and analyzed by LC-MS/MS proteomics. Briefly, IgG-depleted HCCF samples were concentrated to >25 mg/ml using an Amicon Ultra 3 MWCO spin concentrator (Millipore) and verified by BCA assay (Thermo Fisher). Samples were then spiked with bovine serum albumin (Sigma) and adjusted to a final concentration of 2 mg/ml BSA and 20 mg/ml total protein. Protein samples were digested overnight at 37° C. with proteomics-grade trypsin, resulting in a concentration of 0.8 mg/mL for each sample. Samples were concentrated to 2.4 mg/mL, and chromatographically separated using an Aquity UPLC system (Waters). Samples were injected in triplicate (20 μg per injection) onto a Q-Exactive PLUS Mass Spectrometer (Thermo Fisher) operating in data-dependent mode to switch between MS and MS/MS acquisition. Ions generated using a sheath gas flow rate of 40, an auxiliary gas flow rate of 10, a spray voltage of 3 kV, a capillary temperature of 275° C., and an S-Lens RF level of 60. Resolution was set at 70,000 (AGC target 3e6) and 17,500 (AGC target 135) for survey scans and MS/MS events, respectively. The dynamic exclusion duration of 10 s as used with a single repeat count. Peptides searches were conducted against the CHO proteome using Proteome Discoverer software (Thermo Fisher) and spectra analysis was performed to identify hits. Peak signals for 23 proteins of interest were normalized to BSA signal to generate relative expression levels across samples.

Figure 3:
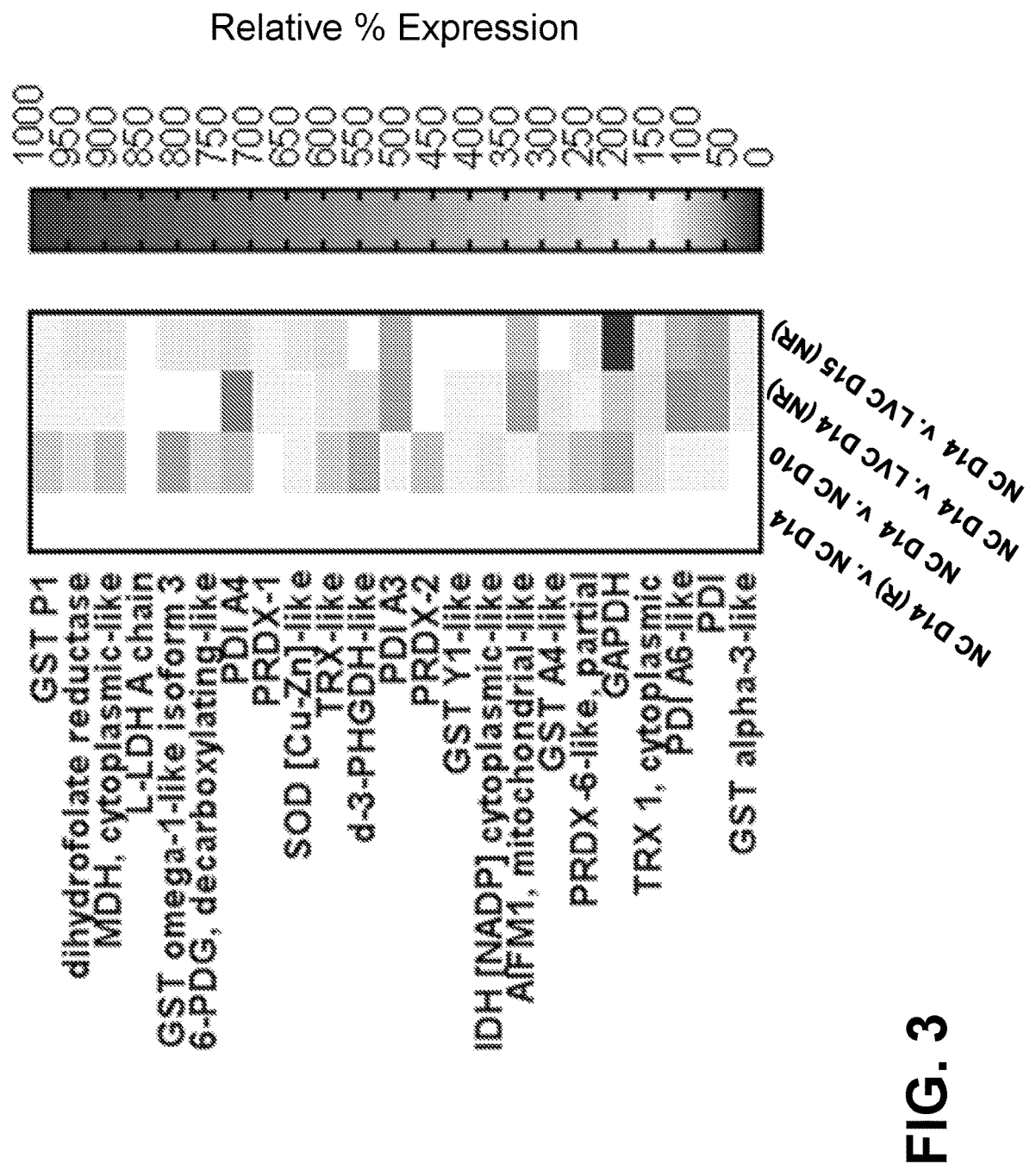
FIG. 3 shows a proteomic analysis of 23 proteins related to redox and apoptosis in samples obtained from normal (NC) cell culture conditions at days 10 and 14 (D10 and D14) and from low viability (LVC) cell culture conditions at days 14 and 15 (D14 and D15). All samples were compared for differential expression against a disulfide-reduced sample (NC D14).

In addition to the two bioreactor samples noted above, one additional sample from each bioreactor was also analyzed for the comparison: a sample from NC at day 10 of the culture (NC D10) and a sample from LVC at day 14 (LVC D14). Expression was normalized to NC D14, with results shown in FIG. 3. In the disulfide reduced sample, thioredoxin (Trx) expression was only 8% higher than LVC D15, whereas protein disulfide isomerase was 34% lower in NC D14. Other reductases, such as peroxiredoxin and dihydrofolate reductase, were detected in both samples in the proteomics screen, with higher levels expressed in the reduced sample. Additionally, two metabolic enzymes 6-phosphogluconate dehydrogenase (6PDG) and glyceraldehyde-3-phosphate dehydrogenase (GAPDH), showed significantly higher expression in NC D14 versus LVC D15 (176% and 999%, respectively). GAPDH was also significantly higher in NC D14 versus LVC D14 (260%). Collectively, these data indicate that increased levels of oxidative stress and increased reductase activity are associated with disulfide bond reduction.

Example 4

Analysis of Trx and TrxR Expression and Activity in Disulfide Reduced and Non-Reduced Samples Based on the proteomics data described in Example 3, the expression of thioredoxin (Trx) and thioredoxin reductase 1 (TrxR) was further analyzed across samples±disulfide bond reduction. Trx and TrxR are involved in oxidative stress responses (primarily within the context of nitric oxide signaling), and the Trx system has been directly implicated in monoclonal antibody reduction in HCCF. Accordingly, the expression of Trx and TrxR in bench, pilot, and manufacturing scale samples from two monoclonal antibodies was analyzed by western blot analysis. Briefly, HCCF materials were analyzed for total protein concentration using a BCA kit (Thermo Fisher). Lysates were normalized to 20 μg total protein and run on 10% or AnyKD PROTEAN TGX Stain-Free gels (Bio-Rad), transferred to polyvinylidene difluoride membranes (Bio-Rad), blocked with 5% bovine serum albumin (Sigma), and probed with a 1:1,000 dilution of a primary antibody against Trx or TrxR (Cell Signaling Technology) overnight at 4° C. Blots were then probed with a 1:20,000 dilution of either horseradish peroxidase-conjugated goat anti-rabbit or goat anti-mouse secondary antibody (Jackson Immunoresearch). Chemiluminescence was visualized using Clarity Western ECL substrate (Bio Rad) on a Chemidoc MP system (Bio-Rad). Band densities were quantitated using Image Lab software (Bio-Rad), and IgG4 light chain was used as a loading control for each blot.

Figure 4A:
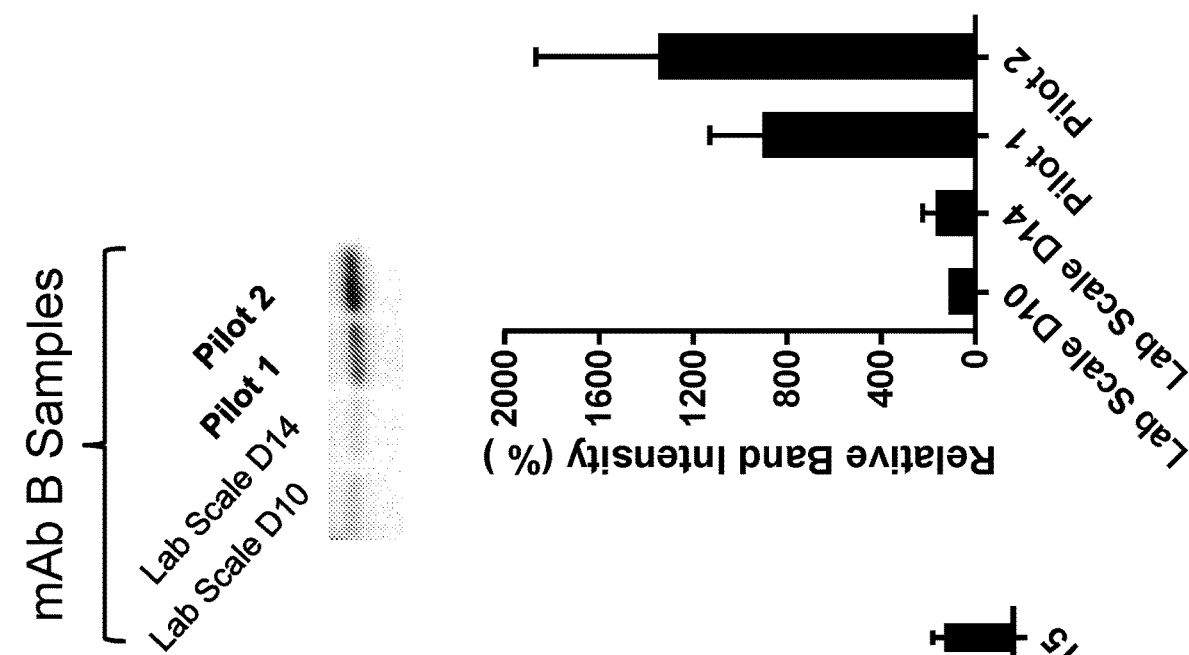
Figure 4B:
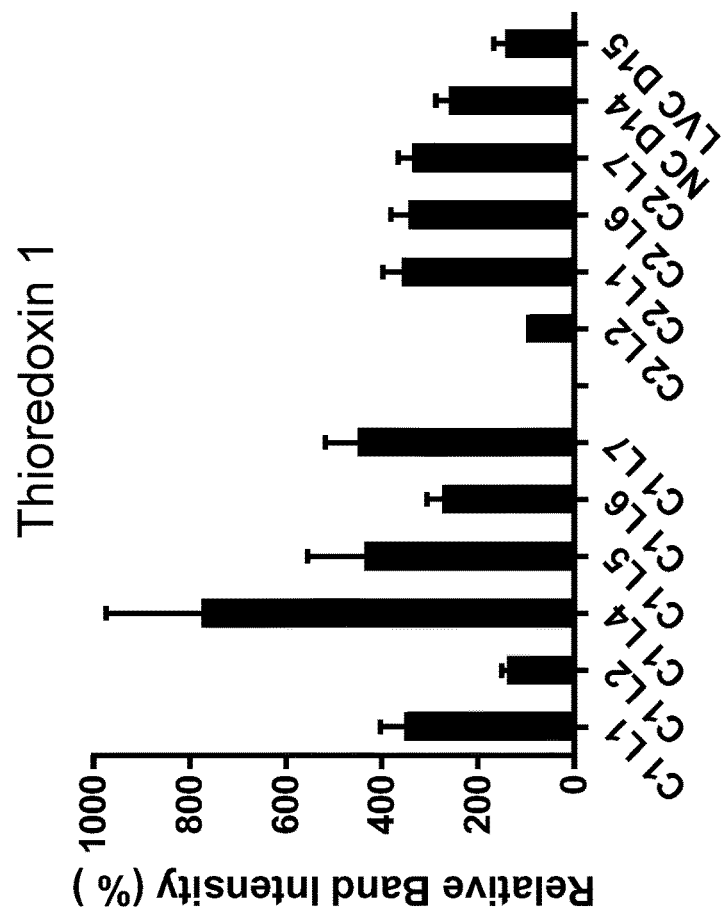

FIG. 4A shows a western blot for Trx expression, and FIG. 4C shows a western blot for and TrxR expression for mAb A and mAb B samples. Relative band intensities were also quantitated for both Trx and TrxR (FIGS. 4B and 4D, respectively). For Trx (FIGS. 4A and 4B), expression ranged from 243±24% to 1332±536% higher in samples that underwent disulfide bond reduction in HCCF relative to samples that did not undergo disulfide bond reduction (C1L2, C2L2, Lab Scale D10, Lab Scale D14). For TrxR (FIGS. 4C and 4D), the magnitude of overexpression in disulfide bond reduction containing samples was lower than Trx, with expression ranging from 229±52% to 430±77% versus non-reducing samples (C1L2, C2L2, Lab Scale D10, Lab Scale D14). However, as with Trx, expression was consistently higher in LMW-forming samples, with the exception of LVC D15, which showed 399±57% expression versus other non-reducing samples.

TrxR activity in HCCF was also measured across samples for both monoclonal antibodies. Briefly, HCCF materials were analyzed for total protein concentration using a BCA kit (Thermo Fisher), and samples were normalized to 5 µg total protein and assayed in triplicate using the thioredoxin reductase assay kit (Sigma), per assay instructions. $A_{412}$ readings were taken at time points from 0-60 minutes. Samples were run in triplicate, and mean±SEM was calculated for each sample point. Results were plotted for each condition according to the following reaction:

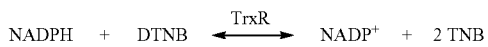

where TrxR activity is measured as a function of TNB absorbance over time.

Figure 5:
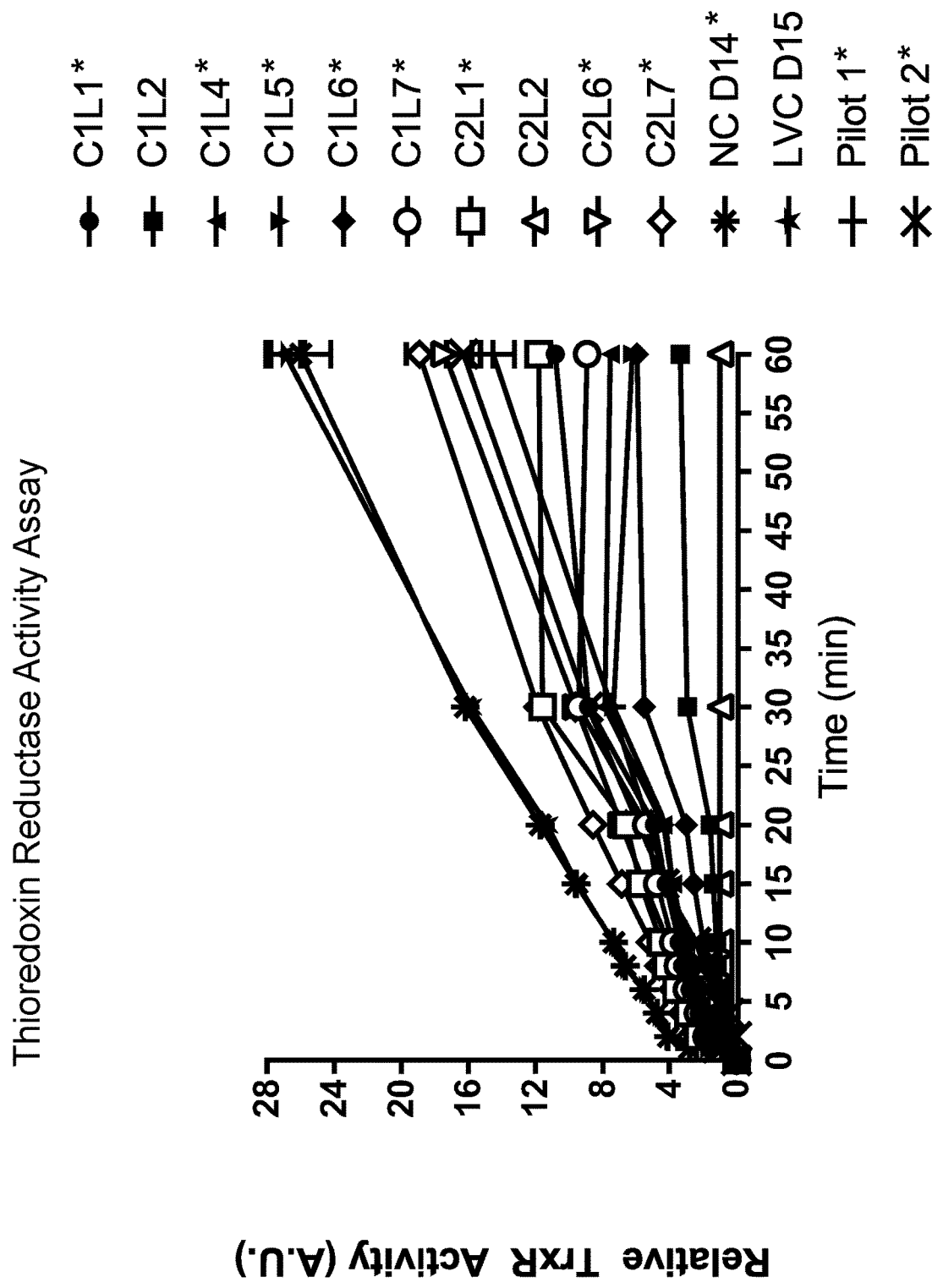
FIG. 5 shows the results of a thioredoxin reductase activity assay for samples harvested from bench, pilot, and manufacturing scale runs for two monoclonal antibodies. Boxed samples demonstrated disulfide bond reduction, while other samples did not.

FIG. 5 shows the results of the TrxR activity assay. Overall TrxR activity was increased 6.0±0.2 to 27.0±1.1 fold in samples containing disulfide bond reduction versus samples that showed no reduction. However sample C1L2, a non-reduction capable sample, showed a modest 3.4±0.2-fold increase in TrxR activity versus C2L2. Additionally, the activity for sample LVC D15, which was also not reduction capable, had some of the highest TrxR activity (27.0±1.1-fold higher than C2L2) of any of the samples tested. Collectively, these data indicate an association between disulfide bond reduction and increased expression and activity of certain enzymes involved in the oxidative stress response.

Example 5

Analysis of G6PD Expression and Activity in Disulfide Reduced and Non-Reduced Samples Given that NADPH is a critical cofactor for TrxR and Trx activity, the expression of glucose-6-phosphate dehydrogenase (G6PD), the first NADPH-generating enzyme in the pentose phosphate pathway, was examined. Samples from two monoclonal antibody cultures were analyzed by western blot (FIG. 6A) and band intensities quantitated (FIG. 6B) according to the procedure described in Example 4 (using a primary antibody against G6PD (Cell Signaling Technology)). While some samples showed approximately 130% expression relative to non-disulfide reduced samples, there was no clear correlation between G6PD expression and disulfide bond reduction.

In order to determine whether G6PD activity was altered in disulfide reduced samples, an ELISA-based test was used to visualize differences in G6PD's ability to generate NADPH. Briefly, HCCF materials were analyzed for total protein concentration using a BCA kit (Thermo Fisher), and samples were normalized to 5 mg/ml total protein and assayed using the G6PD assay kit per kit instructions. Sample fluorescence was measured at 0 and 30 minutes using a Cary Eclipse Fluorescence Spectrophotmeter using a $\lambda_{ex}$ of 540 nm and a $\lambda_{em}$ of 590 nm. Samples were run in triplicate, and mean±SEM was calculated for each sample point. Results were plotted for each condition according to the following reaction:

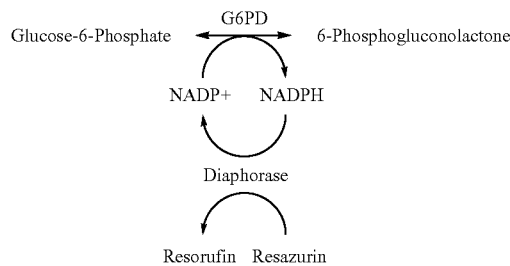

where G6PD activity is measured as increased resorufin fluorescence over time.

As shown in FIG. 7, normalized fluorescence results (relative to C2L2) indicate higher G6PD activity ranging from 3.3±0.2 to 5.5±0.3-fold in those disulfide reduction capable samples than that for C2L2. While the other two non-reduction capable samples, C1L2 and LVC D15, showed a 2.7±0.5 and 2.1±0.3 increase versus C2L2, respectively, the overall G6PD activity in non-reduction capable samples was lower than that in samples showing reduction. Although increased expression of G6PD did not trend with all samples exhibiting disulfide bond reduction, these data indicate a clear association between increased G6PD activity and LMW formation in reduced samples, suggesting a potential regulatory mechanism for increased NADPH production and reductase activity in cells subjected to oxidative stress. Data also suggests that G6PD enzymatic activity may be regulated in the cytosol independently of protein expression during cell culture, offering the potential for increased NADPH production and reductase activity in cells subjected to oxidative stress. While oxidative stress is a likely driver of increased reductase activity in the cytosol and subsequent HCCF during mAb production, further study is needed to confirm this hypothesis.

Example 6

Analysis of GAPDH Expression and Activity in Disulfide Reduced and Non-Reduced Samples GAPDH is known to be a critical cellular stress sensor and may work synergistically with cellular reductase systems to prevent oxidative damage. In the nucleus, GAPDH can also induce gene transcription in response to the metabolic state of the cell. More importantly, GAPDH cysteine residues have shown high sensitivity to the presence of excess peroxides and superoxides leading to its temporary inactivation. This inactivation halts glycolysis, and is the main mechanism that shuttles G6P into pentose phosphate pathway to enable increased NADPH production and subsequent reductase function. When oxidative stress is low, GAPDH is, fittingly enough, reduced by Trx and returned to its active state, thus reactivating glycolysis and decreasing reductase activity.

Figure 8A:
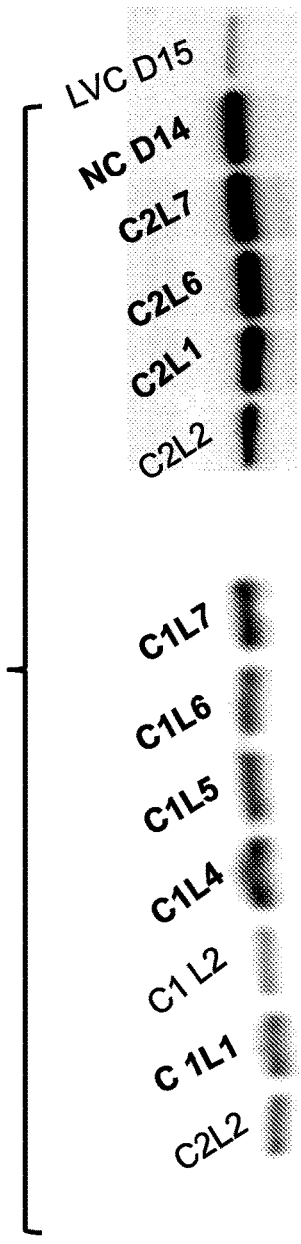
FIGS. 8A and 8B show the expression of glyceraldehyde-3-phosphate dehydrogenase (GAPDH) in samples harvested from manufacturing and lab scale runs for a monoclonal antibody.
Figure 8B:
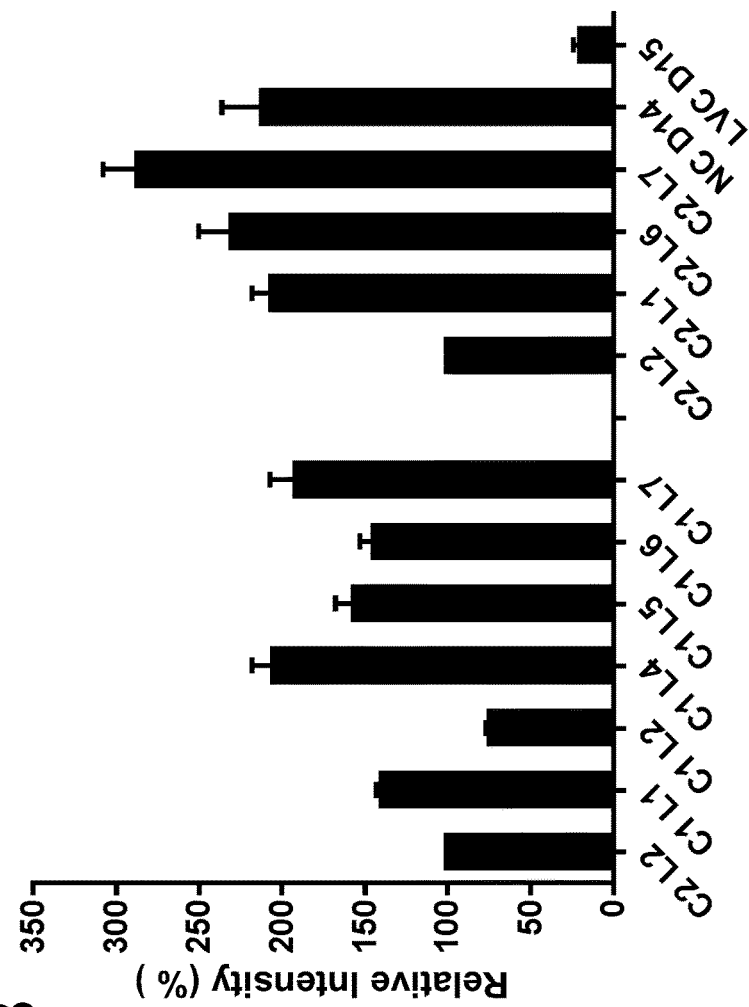

To further visualize GAPDH expression across disulfide reducted and non-reduced samples, HCCF samples from one monoclonal antibody culture were analyzed by western blot (FIG. 8A), and band densities were quantitated (FIG. 8B) according to the procedure described in Example 4 (using a primary antibody against GAPDH (Cell Signaling Technology)). Overexpression of GAPDH ranged from 140±3% to 287±21% in the reduced samples versus non-reduced samples (C1L2 and LVC D15). Whereas the LVC D15 sample showed higher Trx and TrxR expression and activity in prior analysis (FIG. 4), its relative GAPDH expression profile was the lowest among all of the samples and was consistent with the other samples that didn't show disulfide reduction.

To further test whether GAPDH expression in HCCF could be used to predict disulfide bond reduction risk, four samples from three separate cultures of a second monoclonal antibody (Lab Scale D10, Lab Scale D14, Pilot 1 and Pilot 2) were tested by western blot (FIG. 9A), and their band densities were quantitated (FIG. 9B). Pilot 1 and Pilot 2 showed vastly higher expression of GAPDH versus the Lab Scale culture (993±17% to 1822±5%, respectively). HCCF samples from LS D14, Pilot 1, and Pilot 2 were aliquoted and stored under conditions with normal and low $DO_2$ for 24 hours at either 2-8° C. or room temperature, purified, and analyzed by capillary electrophoresis for intact % monomer (FIG. 9C). Results showed that the two samples expressing high levels of GAPDH by western blot also showed significant disulfide bond reduction activity (21% intact monomer for Pilot 1 and 0% intact monomer for Pilot 2), while the sample with very low GAPDH expression (LS D14), showed no disulfide bond reduction under similar storage conditions. These data demonstrate that GAPDH expression can predict disulfide bond reduction in the HCCF across multiple distinct culture samples.

In order to determine whether GAPDH activity was altered in cell samples from bioreactor harvest material, a KDAlert™ GAPDH activity assay (ThermoFisher Scientific) kit was used. The cells were isolated from the bioreactor harvest material, pelleted, and frozen. The frozen cells were thawed on ice and resuspended in PBS. The resuspended cell pellets were lysed in KDAlert™ lysis buffer, followed by protein quantitation using a Pierce™ BCA Protein Assay Kit (ThermoFisher Scientific). Once protein quantitation was determined for each sample, the samples were diluted to contain 20 µg of total protein for use in the KDAlert™ GAPDH activity assay. Following the standard protocol of the activity assay, the samples were transferred to a 96-well plate in triplicate and the KDAlert™ master mix was added in a fluorescence plate reader. The excitation wavelength was 560 nm and the emission wavelength was 590 nm. Samples were measured at the beginning of the assay ($T_0$) and four minutes later ($T_4$). The results were calculated by subtracting $T_0$ from $T_4$. The average of the sample's replicates were used for subsequent calculations.

Figure 10A:
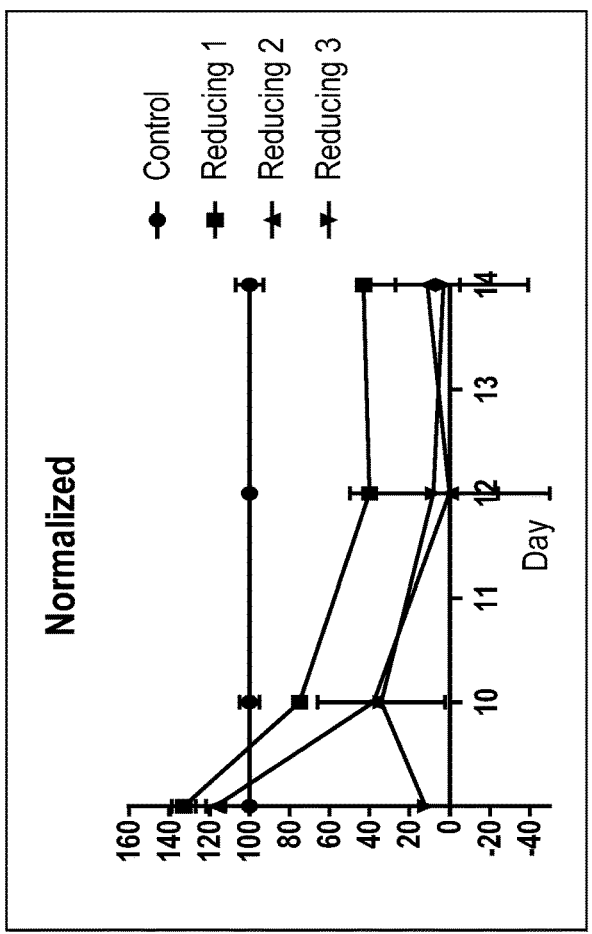
FIGS. 10A and 10B show the results of a glyceraldehyde-3-phosphate dehydrogenase (GAPDH) activity assay for samples harvested from manufacturing-scale runs for a monoclonal antibody.
Figure 10B:
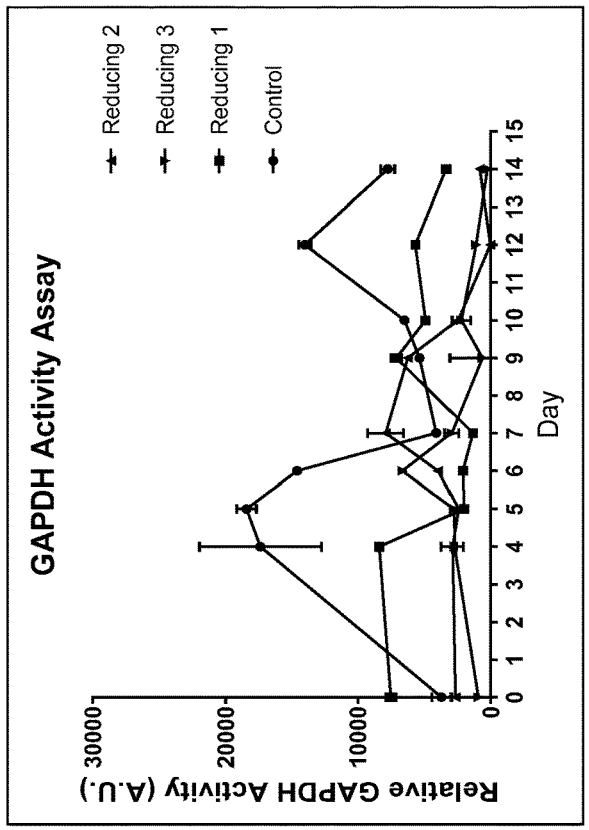

FIG. 10A shows relative GAPDH activity from cells harvested at days 0, 4, 5, 6, 7, 9, 10, 12, and 14 from lab scale bioreactors for mAb B that were cultured under four different conditions: a centerpoint $DO_2$ culture (Control), a variant N-1 centerpoint $DO_2$ condition (Reducing 1), a high cell culture $DO_2$ condition (Reducing 2) and a low cell culture $DO_2$ condition (Reducing 3). FIG. 10B shows the relative data normalized to protein concentration for days 10, 12, and 14 under the same conditions. As shown in FIG. 10B, each sample from day 10 until day 14 had lower levels of GAPDH activity as compared to the control GAPDH sample. Although, FIG. 9B shows a large increase in GAPDH protein expression in HCCF samples from Pilot 1 and 2, FIG. 10B shows that actual GAPDH activity is decreased. Similarly, qPCR data revealed that GAPDH mRNA was increased in the samples that ultimately showed decreased GAPDH activity (data not shown). The decrease in GAPDH activity correlates with a metabolic shift in the cells, which increases the capability for disulfide reduction and LWM formation. Thus, this activity assay allows for early detection of LWM formation, by measuring disulfide reduction, during the protein production phase in the bioreactor.

Example 7

Use of GAPDH Expression to Predict Disulfide Reduction in Bioreactor Cultures

Figure 11B:
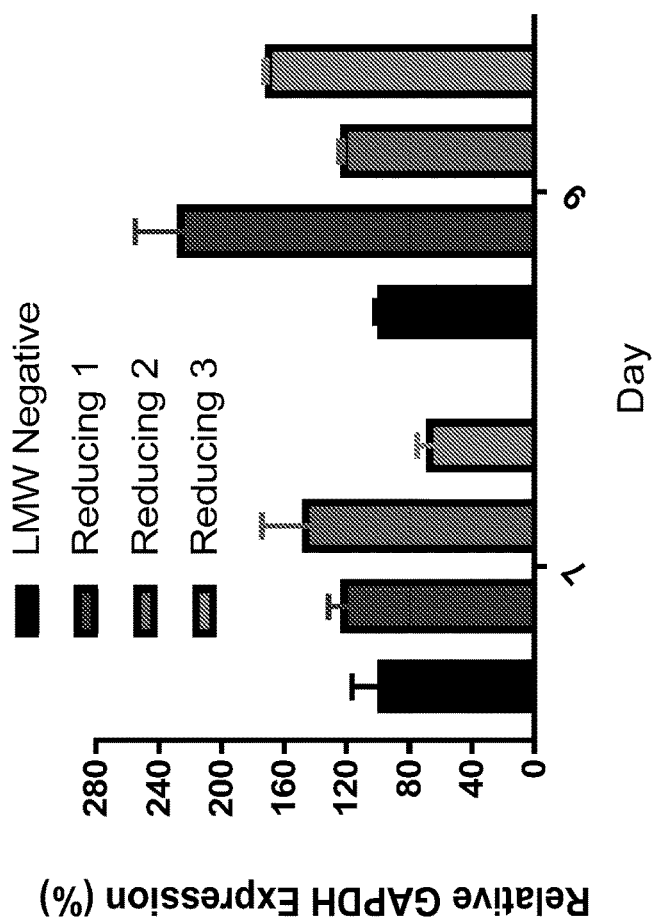
Figure 11A:
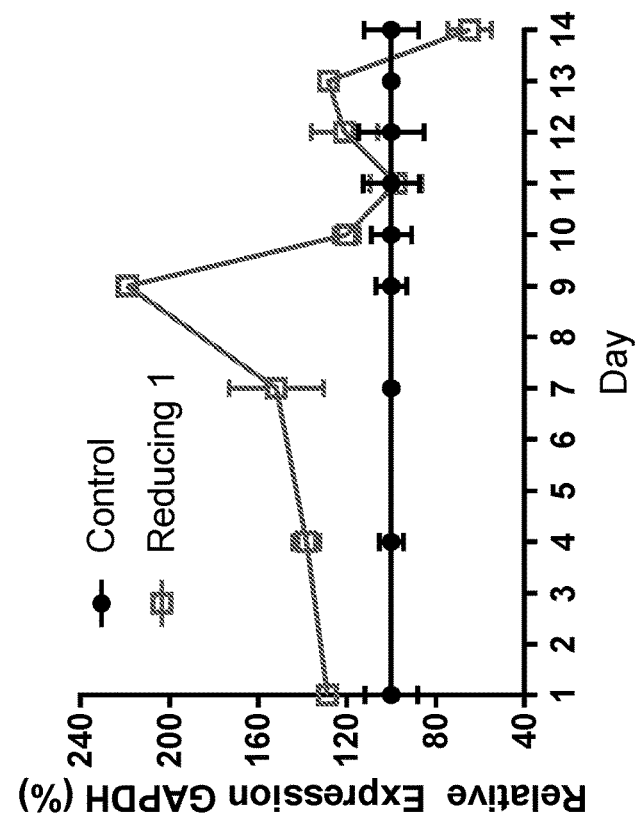

The GAPDH expression during production cell culture was tested under a number of different culture conditions to visualize its temporal expression pattern. Lab scale bioreactors for mAb B were cultured under four different conditions: a centerpoint $DO_2$ culture (Control), a variant N-1 centerpoint $DO_2$ condition (Reducing 1), a high cell culture $DO_2$ condition (Reducing 2) and a low cell culture $DO_2$ condition (Reducing 3). Cells from both the Control and Reducing 1 bioreactor were sampled on day 0, 1, 4, 7, and 9-14 for monitoring the changes to GAPDH expression. Total RNA was isolated from cell pellets for each bioreactor, quantitated spectrophotometrically, normalized to the same starting template concentration for each reaction, and analyzed by q-RT-PCR (FIG. 11A) using the ΔΔCt method. Results of the Reducing 1 condition showed an overall higher trend in relative GAPDH mRNA expression from day 1, starting at 1.3-fold higher than the Control, and steadily increasing to a peak of 2.2-fold higher expression at day 9 before sharply dropping off from day 10-14. To verify these results and test additional reducing bioreactor conditions, cell pellets from a fresh set of Control, Reducing 1, Reducing 2, and Reducing 3 bioreactors were also isolated on day 7 and day 9 of culture and analyzed for GAPDH expression by q-RT-PCR (FIG. 11B). For the Reducing 1 condition, GAPDH expression increased 2.3 fold higher than the Control on day 9. For the Reducing 2 condition, GAPDH expression increased 1.5 fold higher than the Control at day 7, but was only 1.2-fold higher on day 9, while the Reducing 3 condition was 1.7 fold higher than the Control at day 9.

Cell pellets from day 0, day 9, day 12, and day 14 of the Control, Reducing 1, Reducing 2, and days 0, 9, 12, and 13 for Reducing 3 bioreactors used for q-RT-PCR analysis were also analyzed for GAPDH expression by western blot (FIGS. 11C, 11E, 11G, 11I, respectively). Relative band density for each blot was quantitated and plotted (FIGS. 11D, 11F, 11H, 11J, respectively) and each band was normalized to the day 0 level for its respective bioreactor. For the Control (FIGS. 11C and 11D), GAPDH expression levels remained constant throughout the culture. GAPDH expression relative to day 0 increased 325±18% for the Reducing 1 (FIGS. 11E and 11F), 201±11% for the Reducing 2 (FIGS. 11G and 11H), and 171±16% for the Reducing 3 (FIGS. 11I and 11J), all with peak GAPDH expression at day 12.

Figure 12B:
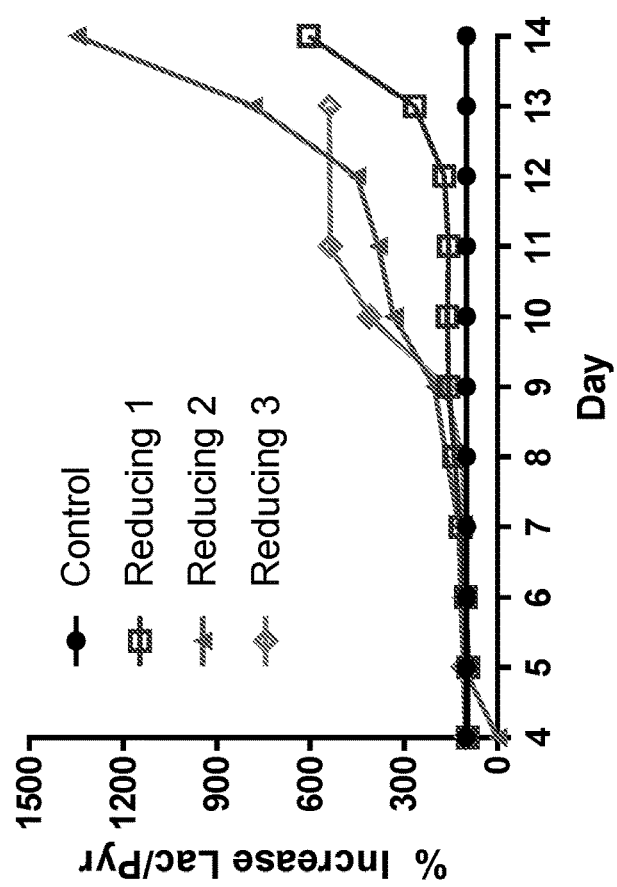
FIGS. 12A and 12B show disulfide reduction analysis for lab scale mAb B batches.
Figure 12A:
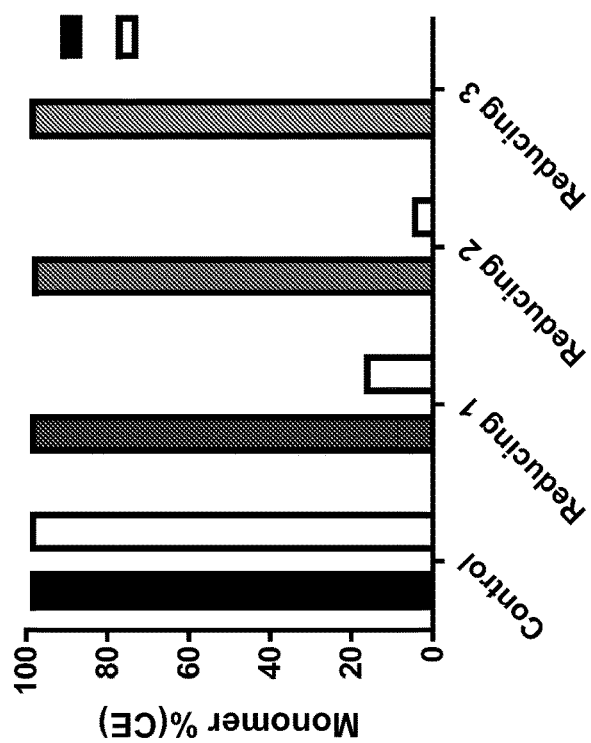

In order to validate the use of GAPDH expression as a marker for disulfide reduction, HCCF from these four bioreactors were split into aliquots and held in the presence or absence of $DO_2$ at 2-8° C. or room temperature for up to 5 days, and capillary electrophoresis was performed on purified samples (FIG. 12A). For the Control condition, no disulfide reduction was detected at 5 days under either storage condition tested. For the Reducing 1-3 conditions, there was no reduction detected in the 2-8° C. samples ("DO") while $DO_2$ was present, however, the monomer was reduced to 16.8, 5.2, and 0.1% for each condition held at room temperature under low $DO_2$ conditions ("NO DO"), respectively. Moreover, increases in lactate production, pyruvate consumption, or both parameters were identified for all the four bioreactor conditions. The molar ratio of lactate to pyruvate (normalized to the Control condition values) was plotted over the course of the 14 day bioreactor run for each condition in FIG. 12B. The Reducing 1 Reducing 2, and Reducing 3 conditions showed increases in the lac/pyr ratio of, 606% on day 14, 1348% on day 14, and 539% on day 13, respectively, relative to Control. All three conditions also showed elevated lac/pyr beginning between day 6 and day 9, relative to Control. The timing of these increases correlates with the timing of both the GAPDH gene and protein expression profiles in FIG. 11.

In all cases of disulfide reduction, results showed that GAPDH protein expression was upregulated versus non-reduction capable samples. The non-reduction capable control showed stable GAPDH gene and protein expression, as well as a consistent lac/pyr molar ratio that was lower relative to the reducing bioreactor conditions. This difference in the lac/pyr profile may be indicative of the different mechanisms that ultimately yield disulfide reduction. One explanation of how low oxygen conditions can lead to a reducing cytosolic environment involves the activity of hypoxia-inducible factor 1 alpha (HIF-1α). During chronic hypoxia, HIF-1α has been shown to produce an excess of reactive oxygen species, thus inducing oxidative stress in the cytosol even under low oxygen conditions.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

The invention claimed is:

1. A method of producing a protein of interest, the method comprising:
    a) culturing host cells capable of producing said protein of interest;
    b) measuring the expression level of a host cell protein, wherein the host cell protein is glyceraldehyde-3-phosphate dehydrogenase (GAPDH); and
    c) isolating said protein of interest if the GAPDH expression level is below a benchmark value, wherein the benchmark value is determined by western blot analysis, wherein the benchmark value is a GAPDH relative band intensity of about 140%, as compared to a non-reduced control sample, wherein said protein of interest is an antibody or antigen-binding fragment thereof.

2. The method of claim 1, wherein the expression level is measured in a cell culture fluid.

3. The method of claim 1, wherein the host cells are mammalian cells.

4. The method of claim 1, wherein the cell culture is a batch, fed batch, or perfusion culture.

5. The method of claim 1, wherein a measurement of the viable cell density, the percent viability of the culture, the lactate level of the culture, the ammonium level of the culture, the titer of the protein of interest, the osmolality of the culture, the amount of dissolved oxygen in the culture, the pCO2 level of the culture, the pH of the culture, the glutamine level of the culture, the glutamate level of the culture, the glucose level of the culture, and/or the expression level of the host cell protein is obtained on a periodic basis.

6. The method of claim 3, wherein the host cells are Chinese Hamster Ovary (CHO) cells.

7. The method of claim 1, wherein the host cells are grown in a bioreactor.

8. The method of claim 5, wherein the measurements are taken during the growth phase of the cell culture.

9. The method of claim 5, wherein said measurements are taken daily.

10. The method of claim 5, wherein the measurements are taken during the transition phase of the cell culture.

11. The method of claim 5, wherein the measurements are taken during the production phase of the cell culture.

12. The method of claim 1, wherein the expression level is measured intracellularly.

13. The method of claim 12, wherein the intracellular expression level is measured in a cell culture lysate.

14. The method of claim 1, wherein the antibody is a chimeric antibody.

15. The method of claim 1, wherein the antibody is a humanized antibody.

16. The method of claim 1, wherein the antibody is a human monoclonal antibody.

17. The method of claim 1, wherein the antibody comprises a heavy chain constant region which is of an IgG isotype.

18. The method of claim 17, wherein the IgG subtype is IgGI, IgG2, IgG3, or IgG4.

19. The method of claim 7, wherein the bioreactor is an N-1 seed bioreactor.

20. The method of claim 7, wherein the bioreactor is used for large-scale production of the protein of interest.

* * * * *